US012735732B2

(12) United States Patent
Jin et al.

(10) Patent No.: US 12,735,732 B2
(45) Date of Patent: Sep. 15, 2026

(54) METHOD FOR PREPARING ULTRA-LOW MOLECULAR WEIGHT DENDROBIUM OLIGOSACCHARIDES BY ENZYMATIC HYDROLYSIS AND ITS APPLICATION

(71) Applicants: Zhejiang A & F University, Hangzhou (CN); Zhejiang Senyu Co., Ltd, Yiwu City (CN)

(72) Inventors: Peng Jin, Hangzhou (CN); Jinping Si, Hangzhou (CN); Qiaoxian Yu, Yiwu City (CN); Dongchao Xie, Hangzhou (CN); Jingjing Liu, Hangzhou (CN); Qizhen Du, Hangzhou (CN)

(73) Assignees: Zhejiang A&F University, Hangzhou (CN); Zhejiang Senyu Co., Ltd, Yiwu City (CN)

( * ) Notice: Subject to any disclaimer, the term of this patent is extended or adjusted under 35 U.S.C. 154(b) by 209 days.

(21) Appl. No.: 18/897,687

(22) Filed: Sep. 26, 2024

(65) Prior Publication Data

US 2025/0011823 A1 Jan. 9, 2025

Related U.S. Application Data

(63) Continuation of application No. PCT/CN2023/116002, filed on Aug. 31, 2023.

(30) Foreign Application Priority Data

Nov. 28, 2022 (CN) ......................... 202211501278.8

(51) Int. Cl.

*C12P 19/04* (2006.01)
*C12N 1/20* (2006.01)
*C12N 9/24* (2006.01)
*C12N 15/70* (2006.01)
*C12R 1/19* (2006.01)

(52) U.S. Cl.

CPC ................ *C12P 19/04* (2013.01); *C12N 1/20* (2013.01); *C12N 9/2402* (2013.01); *C12N 15/70* (2013.01); *C12R 2001/19* (2021.05); *C12Y 302/01* (2013.01)

(58) Field of Classification Search

CPC ......... C12P 19/04; C12N 1/20; C12N 9/2402; C12N 15/70; C12R 2001/19; C12Y 302/01

See application file for complete search history.

(56) References Cited

FOREIGN PATENT DOCUMENTS

| | | | |
|---|---|---|---|
| CN | 101716283 | A | 6/2010 |
| CN | 106868072 | A | 6/2017 |
| CN | 108823261 | A | 11/2018 |
| CN | 113337528 | A | 9/2021 |
| CN | 114774392 | A | 7/2022 |
| CN | 116024286 | A | 4/2023 |
| WO | 2022183763 | A1 | 9/2022 |

*Primary Examiner* — Robert J Yamasaki
*Assistant Examiner* — Trevor Kane
(74) *Attorney, Agent, or Firm* — IPro, PLLC; Na Xu

(57) ABSTRACT

The disclosure provides a method for preparing ultra-low molecular weight *Dendrobium* oligosaccharides by enzymatic hydrolysis and its application, and belongs to the technical field of bioengineering. In the disclosure, *Thermobifida halotolerans*-derived glycosidases are recombined to an *Escherichia coli* expression system to realize high activity expression. The recombinantly expressed ThDPS enzyme can hydrolyze *Dendrobium* polysaccharides, and produced oligosaccharide products mainly include ultra-low molecular weight (<1000 Daltons) *Dendrobium* disaccharides, *Dendrobium* trisaccharides, *Dendrobium* tetrasaccharides and *Dendrobium* pentasaccharides, and low-molecular weight (<10000 Daltons) *Dendrobium* hexaoses, *Dendrobium* heptaoses and *Dendrobium* octacoses, and higher *Dendrobium* oligosaccharide products. The disclosure further provides application of *Dendrobium* oligosaccharides prepared by enzymatic hydrolysis in promoting proliferation of lactic acid bacteria, laying a technical foundation for the biological preparation of the ultra-low molecular weight *Dendrobium* oligosaccharides by enzymatic hydrolysis and the development of prebiotics, and being suitable for industrial production and application.

11 Claims, 11 Drawing Sheets

Specification includes a Sequence Listing.

METHOD FOR PREPARING ULTRA-LOW MOLECULAR WEIGHT DENDROBIUM OLIGOSACCHARIDES BY ENZYMATIC HYDROLYSIS AND ITS APPLICATION

REFERENCE TO SEQUENCE LISTING

The instant application contains a Sequence Listing in XML format as a file named "3050-YGHY-2023-33.xml", created on Sep. 14, 2024, of 16156 bytes in size, and which is hereby incorporated by reference in its entirety.

TECHNICAL FIELD

The disclosure relates to a method for preparing ultra-low molecular weight *Dendrobium* oligosaccharides by enzymatic hydrolysis and its application, and belongs to the technical field of bioengineering.

BACKGROUND

*Dendrobium officinale* Kimura et Migo (*D. officinale*) is a precious traditional medicinal material of *Dendrobium* genus, Orchidaceae, including more than 1500 species of plants. It is currently listed in the catalogue of homology of medicine and food. With the improvement of people's living standards and quality, the application demand of traditional Chinese medicinal materials is becoming more and more extensive. The chemical composition and pharmacological activity of *D. officinale* are currently the hot spots and focus in the field of *Dendrobium* research. It has been shown by a large number of pharmacological activity studies that *D. officinale* has immunomodulatory, antitumor, anti-mutation, antihypertensive, hypolipidemic, hypoglycemic, antiviral, anti-oxidant, anti-radiation, anti-ulcer, anti-aging and other effects. In addition to medicinal use, *Dendrobium* has been used as a health food for thousands of years. Therefore, these active ingredients have great prospects for the development of finished Chinese patent medicine preparations and health-care products in terms of improving immunity, aging resistance, fatigue resistance, etc. In recent years, nearly 100 active compounds have been isolated from more than 40 species of *Dendrobium* with pharmacological activity, including: *Dendrobium* polysaccharides, dendrobine, polyphenols, amino acids, flavonoids, terpenoids and trace elements.

At present, the most widely studied active ingredient of the *Dendrobium* polysaccharide is polysaccharide, where *D. officinale* polysaccharide (DOP) is mainly glucomannan formed by mannose and glucose through a glycosidic bond. According to research findings, *D. officinale* polysaccharide has the activities of protecting gastric mucosa, regulating blood sugar, protecting liver, enhancing immunity, reducing blood fat and the like. In recent years, according to research findings, the low-molecular weight polysaccharide has higher biological activities. For example, low-molecular weight mannan oligosaccharides can also stimulate the liver to secrete mannan-binding protein, activate a complement system to play a role of conditioning and natural anti-infectious immunity, and have very good effects of recognition, adhesion and elimination of enteropathogenic microorganisms. Due to the high-molecular weight and high viscosity of natural *Dendrobium* polysaccharides, their use in the fields of medicine and food processing is limited. The glycosidic bond of the *Dendrobium* polysaccharide is easy to break in an acidic solution, forming hydrolysates with different degrees of polymerization. Therefore, acid catalyzed hydrolysis is a commonly used method for degrading plant polysaccharides. *D. officinale* polysaccharide is hydrolyzed under hydrolysis with sulfuric acid, trifluoroacetic acid, and hydrochloric acid assisted by heating with a boiling water bath or direct high-temperature heating with a heating device, and thus, long time is consumed, the acid concentration is high, the heating device is easy to be damaged, and the costs are high. The trifluoroacetic acid and the hydrochloric acid are highly volatile, irritating to the respiratory system, and toxic, and their concentrations are difficult to control during operation, so they are not suitable for large-scale hydrolysis of polysaccharides to prepare mannose. The recently reported technology for preparing low-molecular weight *Dendrobium* polysaccharides using fungal fermentation of the *Dendrobium* polysaccharide has been developed, but its fermentation time is long, reaction products are complex and difficult to isolate, and the prepared molecular weight is 10000 Da or more. Therefore, industrial production requirements are difficult to meet. As a result, these factors have led to high production costs for pharmaceutical-grade and food-grade oligosaccharides.

SUMMARY

In order to address the numerous shortcomings in the preparation of small molecule active oligosaccharides in *Dendrobium* polysaccharides, biologically enzymatic hydrolysis is employed in the disclosure to catalyze and degrade the *Dendrobium* polysaccharides. Due to mild reaction conditions of biologically enzymatic hydrolysis, high specificity, and high product purity, industrial production preparation is easy to realize.

The disclosure provides application of *Thermobifida halotolerans*-derived glycosidases or recombinant microorganisms expressing the glycosidases in hydrolyzing *Dendrobium* polysaccharides.

In an embodiment, the *T. halotolerans*-derived glycosidase has an amino acid sequence shown in SEQ ID NO.3.

In an embodiment, a gene encoding the glycosidase has a nucleotide sequence shown in SEQ ID NO.1 or SEQ ID NO.2.

In an embodiment, the microorganism includes but is not limited to *Escherichia coli*.

The disclosure further provides a method for preparing ultra-low molecular weight *Dendrobium* oligosaccharides, where the method is to use the glycosidase or a cell culture containing the glycosidase for degrading *Dendrobium* polysaccharides.

In an embodiment, the molecular weight of the ultra-low molecular weight *Dendrobium* oligosaccharide is ≤1000 Da, including but not limited to *Dendrobium* disaccharides, *Dendrobium* trisaccharides, and *Dendrobium* tetrasaccharides.

In an embodiment, the method is to add the glycosidase or the cell culture containing the glycosidase to a high-molecular weight *Dendrobium* polysaccharide solution.

In an embodiment, the cell culture is a glycosidase-containing fermentation broth obtained by culturing recombinant microorganisms expressing the glycosidase in a medium for a period of time.

In an embodiment, the cell culture is a crude enzyme solution obtained by culturing recombinant *E. coli* expressing the glycosidase in a medium for a period of time, and collecting and crushing bacterial cells.

In an embodiment, the molecular weight of the polysaccharide in the high-molecular weight *Dendrobium* polysaccharide solution is $\geq 1\times10^4$ Da.

In an embodiment, the molecular weight of polysaccharides in the high-molecular weight *Dendrobium* polysaccharide solution is $1\times10^4$-$1\times10^7$ Da.

In an embodiment, the *Dendrobium* polysaccharide is formulated into a solution with a concentration of 1-100 g/L with a phosphate buffer of 50 mM and pH 7.0.

In an embodiment, the concentration of the *Dendrobium* polysaccharide in the solution is 10 g/L.

In an embodiment, the addition amount of the glycosidase is ≥1 $U/g_{Dendrobium\ polysaccharide}$, specifically, 1-1000 $U/g_{Dendrobium\ polysaccharide}$ or 500 $U/g_{Dendrobium\ polysaccharide}$.

In an embodiment, the glycosidase involved in the degradation of the *Dendrobium* polysaccharide is a pure enzyme solution without other salts, and the concentration of the enzyme in a reaction system is 10-10000 U/L, specifically, 5000 U/L.

In an embodiment, a pH value of a solution in the reaction system is controlled to be 5.0-10.0, specifically, 7.0.

In an embodiment, the temperature of the reaction system is 10° C.-75° C., specifically, 60° C.

In an embodiment, the reaction time of the reaction system is 0.5-16 h, specifically, 2 h.

In an embodiment, the temperature of the reaction system is 30° C.-45° C., specifically, 37° C.

In an embodiment, the reaction time is ≥45 min, or ≥4.5 h, or ≥12 h.

The disclosure further provides application of the glycosidase or the method in producing products containing *Dendrobium* oligosaccharides.

In an embodiment, the high-molecular weight *Dendrobium* polysaccharide can be hydrolyzed into ultra-low molecular weight *Dendrobium* oligosaccharides of ≤1000 Daltons, including but not limited to *Dendrobium* disaccharides, *Dendrobium* trisaccharides, *Dendrobium* tetrasaccharides and *Dendrobium* pentasaccharides, or the high-molecular weight *Dendrobium* polysaccharide can be hydrolyzed into *Dendrobium* hexaoses, *Dendrobium* heptaoses, *Dendrobium* octacoses and more units oligosaccharides of 1000 to 10000 Daltons, and oligosaccharides of 10000 Daltons or more.

The disclosure also claims protection for hydrolyzed *Dendrobium* oligosaccharides prepared by applying the method.

The disclosure also claims protection for application of the hydrolyzed *Dendrobium* oligosaccharides in promoting proliferation of probiotics.

In an embodiment, the application is not intended for the treatment of diseases.

In an embodiment, the probiotics include but are not limited to *Lactobacillus plantarum, Streptococcus thermophilus, Lactobacillus reute, Lactobacillus casei, Lactobacillus rhamnosus*, and *Lactobacillus paracasei*.

Beneficial Effects (1) The disclosure provides application of *T. halotolerans*-derived glycosidases in hydrolyzing *Dendrobium* polysaccharides.

(2) In the disclosure, the *T. halotolerans*-derived glycosidase is heterologously expressed in recombinant *E. coli*, and a ThDPS expression product with significantly improved expression activity is obtained by optimizing an encoding gene of the glycosidase, thereby realizing the high-efficiency activity expression of ThDPS enzymes. Since *E. coli* has strong protein expression ability, the large-scale fermentation preparation of the ThDPS enzymes is facilitated. The thermophilic glycosidase ThDPS recombinantly expressed in the disclosure can be directly used for the efficient hydrolysis of the *Dendrobium* polysaccharides, thereby realizing the large-scale enzymatically catalytic preparation of active oligosaccharides.

(3) In the disclosure, the enzyme prepared by the fermentation of genetically engineered strains is directly used for degrading the *Dendrobium* polysaccharides to prepare oligosaccharide small molecules, having extremely simple reaction conditions, having no requirement for instruments, and being implemented at room temperature and pressure. The enzymatic hydrolysis process does not require the addition of any organic reagents, without generating any pollution or waste. The conversion yield of small molecule oligosaccharides is 95% or more, and the minimum molecular weight is 3.69 kDa. The product is relatively simple in an aqueous solution, and is easy to purify and recover. Based on application analysis, the method of the disclosure has a very wide value for preparing single active functional oligosaccharide and its derivatives in industry.

(4) The disclosure further provides application of *Dendrobium* oligosaccharides prepared by hydrolysis through thermophilic mannosidase THDPS in promoting proliferation of lactic acid bacteria, where the *Dendrobium* oligosaccharides can increase the number of *L. plantarum* by 34.8% in comparison with that of a control group, and facilitates the development of new prebiotics.

DETAILED DESCRIPTION

Figure 1:
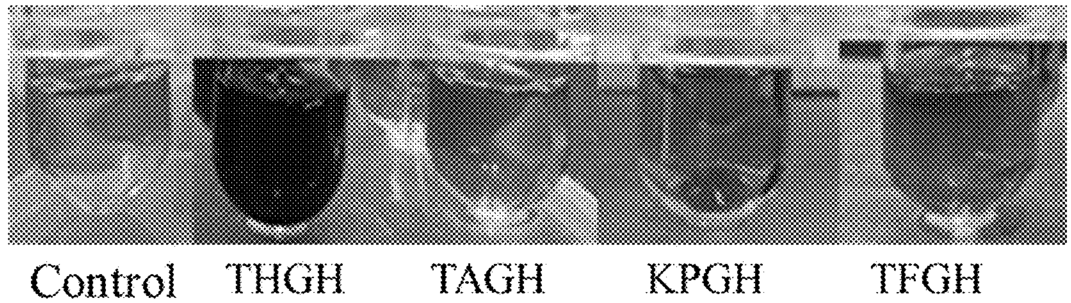
FIG. 1 shows results of a DNS method for detecting the activity of *Dendrobium* polysaccharides hydrolyzed by multiple glycoside hydrolases.

An Expression Host and Medium of ThDPS Glycosidases are as Follows:

Plasmid pET21a and *E. coli* BL21 (DE3) involved in the following examples are purchased from Stratagene, La Jolla, CA, USA.

LB liquid medium: yeast powder 5 g/L, peptone 10 g/L, sodium chloride 10 g/L, and ampicin concentration 100 μg/mL.

LB solid medium: yeast powder 5 g/L, peptone 10 g/L, sodium chloride 10 g/L, ampicin concentration 100 μg/mL, and agar 15 g/L.

M17 liquid medium (g/L): soytone 5.0, peptone 5.0, casein peptone 2.5, yeast extract powder 2.5, beef extract powder 5.0, lactose 5.0, sodium ascorbate 0.5, sodium β-glycerophosphate 19.0, and magnesium sulfate 0.25.

Usage: Heating 42.3 g of the liquid medium and dissolving it in 1 L of distilled water, and sterilizing under a high pressure at 121° C. for 15 min for later use.

M17 solid medium (g/L): soytone 5.0, peptone 5.0, casein peptone 2.5, yeast extract powder 2.5, beef extract powder 5.0, lactose 5.0, sodium ascorbate 0.5, sodium β-glycerophosphate 19.0, magnesium sulfate 0.25, plus agar 15 g/L.

Usage: Same as M17 liquid medium, sterilizing under a high pressure at 121° C. for 15 min for later use.

ThDPS Glycosidase Activity Determination:

Enzymatic activity definition: the amount of enzyme that can convert 1 micromole of substrate per 1 minute at 37° C. is defined as one unit of enzymatic activity (U).

Enzymatic activity determination: ThDPS glycosidases can decompose *Dendrobium* polysaccharides into mannan oligosaccharides. The mannan oligosaccharide has reducibility and can undergo a certain chemical reaction with a DNS reagent under alkaline conditions to generate 3-amin-5-nitrosalicylic acid that is brownish-red under boiling conditions. The amount of reducing sugar generated can be measured with a spectrophotometer. The gradation of the color of the acid is related to the content of the reducing sugar.

Specific steps for enzymatic activity determination are as follows: a total reaction system is 2 mL, containing 1 mL of a *Dendrobium* polysaccharide solution with a concentration of 4 g/L, 200 μL of a phosphate buffer with a concentration of 200 mM, and 10 μL of an enzyme solution. 10 μL of distilled water is added to a control group, and water is replenished to a total volume of 2 mL for all reaction solutions. A mixed reaction solution is incubated at 37° C. for 30 min. After being taken out, the incubated mixed reaction solution is placed in a boiling water bath for 1 min to inactivate the enzymes. 2 mL of a DNS solution is added into each tube, and the tube is placed in the boiling water bath for 3 min, and then is rapidly cooled, and 1 mL of distilled water is added to make up to 5 mL. The absorbance is measured at the wavelength of 540 nm to determine the enzymatic activity.

Gel Fluorescence Electrophoresis of Hydrolysate *Dendrobium* Oligosaccharides:

Reagent preparation: DMSO (acetic acid: water: DMSO=3:17:20), 0.2 M ANTS (dissolved in water, water: acetic acid=17:3), 1 M NaCNBH3 (dissolved in a DMSO solution) are formulated.

Sample treatment: an aqueous solution of 80 μl of an oligosaccharide hydrolysate and 80 μL of sucrose is placed in EP tubes. 10 μL of DMSO, 5 μL of ANTS and 5 μl of $NaCNBH_3$ are accurately aspirated into each EP tube with a pipette, and the EP tubes are placed in a water bath kettle at 40° C. and water-bathed for 16 h. An oven is set to 45° C., and a cover of each EP tube is opened and the EP tubes are placed in the oven for 6 h. When the sample volume is reduced to half of the original volume, 3 M 100 μl urea is added to samples, and 6 M 10 μL urea is added to standard samples. Shaking and fair mixing are carried out, and the mixture is placed overnight in a refrigerator at −20° C.

Preparation of separation glue: 5.33 mL of 30% acrylamide, 1 mL of 1.5 M Tirs-HCl (pH 8.8), 1.67 mL of distilled water, 30 μL of 10% ammonium persulfate and 10 μL of TEMEO are well mixed to prepare glue.

After electrophoresis, the taken-out gel is placed under a UV lamp to observe bands.

Determination of Prebiotics Effect of Active *Dendrobium* Oligosaccharides:

Extraction and separation of *Dendrobium* polysaccharides: the *Dendrobium* plants are dried, ground and sieved, and then the dried, ground and sieved *Dendrobium* plants are extracted with hot water at 60° C. for 4 h or more at a certain solid-liquid ratio. After that, centrifugation is carried out at 8000×g and a supernatant is taken, and 3 times the volume of absolute ethanol is added, and the mixture is placed in a refrigerator at 4° C. for ethanol precipitation overnight. Afterwards, centrifugation is carried out at 8000×g to obtain precipitates. An appropriate amount of pure water is added to dissolve the precipitates, and then centrifugation is carried out to remove insoluble impurities. Ethanol precipitation is carried out again to obtain crude *Dendrobium* polysaccharides.

Obtaining of active small molecular oligosaccharides: under certain conditions, *Dendrobium* oligosaccharides with different sizes are obtained by hydrolysis with genetic engineering strain hydrolase, and the degree of hydrolysis of the *Dendrobium* oligosaccharide is preliminarily determined by a DNS method, and then the hydrolysis and molecular weight are detected by gel fluorescence electrophoresis combined with high performance liquid chromatography. Afterwards, the active *Dendrobium* oligosaccharides are preliminarily sterilized in a boiling water bath for 5 min, and then the preliminarily sterilized *Dendrobium* oligosaccharides are placed under a UV lamp for 5 min or more. The active *Dendrobium* oligosaccharides are placed in a refrigerator at 4° C. for later use.

Determination of prebiotics effect of active *Dendrobium* oligosaccharides: The *Dendrobium* oligosaccharides are added at an addition amount of 5% into an MRS medium, a basal medium of lactic acid bacteria, and an equal amount of sterile water is used as a blank control. After anaerobic activation of preserved lactic acid bacteria at 37° C., 100 μL of bacterial solution is added into a sterilized medium and undergoes static culture at 37° C. The absorbance of the bacterial solution, i.e., the concentration of the bacterial solution at 600 nm is determined to reflect its growth status and demonstrate the prebiotics activity of the *Dendrobium* oligosaccharides.

Extraction and Determination of *Dendrobium* Polysaccharides:

Extraction of *Dendrobium* polysaccharides: dried *Dendrobium* samples are crushed by a crusher, and the crushed sampled are poured into a beaker after being sieved. 500 times the volume of distilled water (material ratio: 1:500) is added for water extraction at 60° C. for 1 h. Then, suction filtration is carried out on a liquid extract and the solution is retained. Filter residues are further extracted once (material ratio: 1:300). After being merged, the filtrate is subjected to vacuum rotary concentration by a rotary evaporator to 200 mL. A concentrated solution and absolute ethanol (volume ratio: 1:3) are well mixed, and then the mixture is placed in a refrigerator at 4° C. and stands overnight for precipitation. After overnight, the polysaccharides obtained after ethanol precipitation is centrifuged at the rotating speed of 8000×g for 6 min. The supernatant is discarded and precipitates are retained. After water is added to dissolve the precipitates and impurities are removed, the supernatant is retained. Three times the volume of ethanol is further added for static ethanol precipitation, and centrifugation is carried out for 6 min. Finally, after water-insoluble impurities are removed, three times the volume of ethanol is also added for static ethanol precipitation, and centrifugation is carried out for 10 min. After ethanol precipitation for three times, the supernatant is removed, and the precipitates are retained. Powder is prepared after the ethanol volatilizes or the precipitates are dried in the oven at 50° C., and the powder is sealed in a refrigerator at 4° C. for later use.

Determination of Monosaccharide Composition of *Dendrobium* Oligosaccharides:

Reagent formulation: 15 mM NaOH solution: 2.4 g 50% NaOH solution, and 2 L water; and 15 mM NaOH and 100 mM NaOAC solution: 1.2 g 50% NaOH solution, 8.2 g NaOAC, and 1 L water.

Formulation and calculation method for a standard solution: 16 monosaccharide standards (fucose, rhamnose, arabinose, galactose, glucose, xylose, mannose, fructose, ribose, galacturonic acid, glucuronic acid, galactosamine hydrochloride, glucosamine hydrochloride, N-acetyl-D-glucosamine, guluronic acid, and mannuronic acid) are taken and formulated into standard mother solutions. Precisely formulated concentration standards of various monosaccharide standard solutions are taken as mixed standards. According to an absolute quantitative method, the mass of different monosaccharides is determined, and the molar ratio is worked out according to the molar mass of monosaccharides.

Sample preparation: 200 μL sample is precisely measured and placed in an ampoule bottle. 2 ml of 3 M TFA is added, and hydrolyzation is carried out at 120° C. for 3 h. An acid hydrolysis solution is accurately sucked and transferred into a tube, and is blow-dried with nitrogen. 1 ml of water is added and swirled and fair mixing is carried out. 50 μL of mixture is sucked, and is added into 950 μl of deionized water, and centrifugation is carried out at 12000 rpm for 5 min. The supernatant is taken for IC analysis.

Chromatographic method: Chromatographic column: Dionex Carbopac™ PA20 (3*150 mm); mobile phase: A: H2O; B: 15 mM NaOHC; 15 mM NaOH and 100 mM NaOAC; flow rate: 0.3 ml/min; injection volume: 5 μL; column temperature: 30° C.; and detector: electrochemical detector.

Molecular Weight Determination of *Dendrobium* Oligosaccharides:

Molecular weight distribution and determination: the sample solutions of the *Dendrobium* oligosaccharides with different degrees of hydrolysis are diluted to 4 mg/mL, with 2 mL per group, and filtration is carried out with a 0.22 um filter membrane for later use. Preparation of control solution for polysaccharide content determination: a Pullulan standard with an average molecular weight of $8.05\times10^5$ Da is accurately weighed, to the accuracy of 1.0 mg. The Pullulan standard is formulated with a mobile phase into a series of control solutions with mass concentrations of 2 mg/ml, 1.25 mg/ml, 1 mg/ml, 0.75 mg/ml, 0.5 mg/ml, 0.25 mg/ml, 0.1 mg/mL, 0.05 mg/mL, and 0.01 mg/mL, and filtration is carried out with a 0.45 μm filter membrane to obtain the control solution. High performance gel chromatographic columns are Xtimate™ SEC-1000 (7.8×300 mm, 5 μm) and Xtimate™ SEC-300 (7.8×300 mm, 5 μm). The two columns are connected in series, the mobile phase is double distilled water, the injection volume is 10 μL, the flow rate is 1.0 mL/min, the detector is a differential refraction detector (RID), and the column temperature is 35° C. The formulated Pullulan standard solutions with different relative molecular weights are analyzed by HPGFC. By taking LogMw as the ordinate, and the retention time as the abscissa, the linear regression equation is $Y=-0.307\ 6X+9.697\ 1$, $R^2=0.9938$. The hydrolyzed *Dendrobium* oligosaccharide solutions prepared in the examples are analyzed under the same chromatographic conditions.

Example 1: Heterologous Expression and Preparation of Recombinant *E. coli* with Various Glucosidases 1) Recombinant Construction of Glycosidase Gene In order to screen glycosidases that can efficiently hydrolyze *Dendrobium* polysaccharides, encoding genes of glycoside hydrolases from different species and different glycosidase families were screened by bioinformatics comparison, and then through phylogenetic tree and conservative site comparison analysis, 4 representative glycoside hydrolases were selected for heterologous recombinant expression to prepare glycoside hydrolase proteins.

By taking *T. halotolerans*-derived THGH (shown in SEQ ID NO.1), a *Thermobifida fusca*-derived TFGH gene sequence (GenBank accession number: AID15578.1, as shown in SEQ ID NO.4), *Klebsiella pneumoniae*-derived KPGH (GenBank accession number: CP035202.1 (146142-148334, as shown in SEQ ID NO.5)) and *Thermobifida alba*-derived TAGH (GenBank accession number: BBA57841.1, as shown in SEQ ID NO.6) as templates, PCR amplification was carried out on the encoding genes. pET21a was recombined by seamless cloning, and the recombinant plasmid THGH-pET21a, the recombinant plasmid TFGH-pET21a, the recombinant plasmid KPGH-pET21a and the recombinant plasmid TAGH-pET21a transformed *E. coli* BL21 (DE3) to obtain recombinant bacteria THGH-pET21a/BL21 (DE3), TFGH-pET21a/BL21 (DE3), KPGH-pET21a/BL21 (DE3), and TAGH-pET21a/BL21 (DE3), respectively. An appropriate amount of transformed solution was coated on an LB medium plate, and cultured overnight at 37° C. After colony PCR was correct, single colonies were selected for shake-flask culture and plasmid was extracted. After the correctness is verified by further sequencing, a strain containing the recombinant plasmid was the recombinant bacterium, and further expression was carried out.

2) Induced Expression and Activity Detection of Proteins of Recombinant Bacteria The recombinant bacteria constructed in step 1 were inoculated into a test tube containing 5 mL of LB medium (containing 100 ug/mL ampicillin), and underwent shake-flask culture at 37° C. and 200 r/min for 16 h. As a seed solution, the cultured bacterial solution was transferred into 100 mL of LB liquid medium (containing 100 ug/mL ampicillin) with an inoculum size of 1%, and underwent shake-flask culture at 37° C. and 200 rpm until OD600 was 0.6. 0.1 mM of IPTG was added to induce expression, and shaking culture was carried out for 24 h at 37° C. and 200 rpm. The obtained fermentation broth was centrifuged at 8000×g and 4° C. for 10 min, the supernatant was removed, and bacterial cells were collected. The bacterial cells were resuspended with 8 mL of 50 mM PBS of pH=7.0. After ultrasonic crushing, centrifugation was carried out for 10 min at 4° C. and 12000×g, precipitates were removed, the supernatant was collected for the hydrolysis reaction of *Dendrobium* polysaccharides, and hydrolysis products were detected by using a DNS method. According to the results shown in FIG. 1, only THGH expression products have significant hydrolysis activity on the *Dendrobium* polysaccharides, and a large amount of reducing oligosaccharides are produced, and the enzymatic activity reaches 68 $U/OD_{bacterial\ cells}$. However, several other glycosidases do not show significant hydrolysis activity.

Example 2: Optimized Expression of ThDPS *Dendrobium* Polysaccharide Hydrolases

Figure 2:
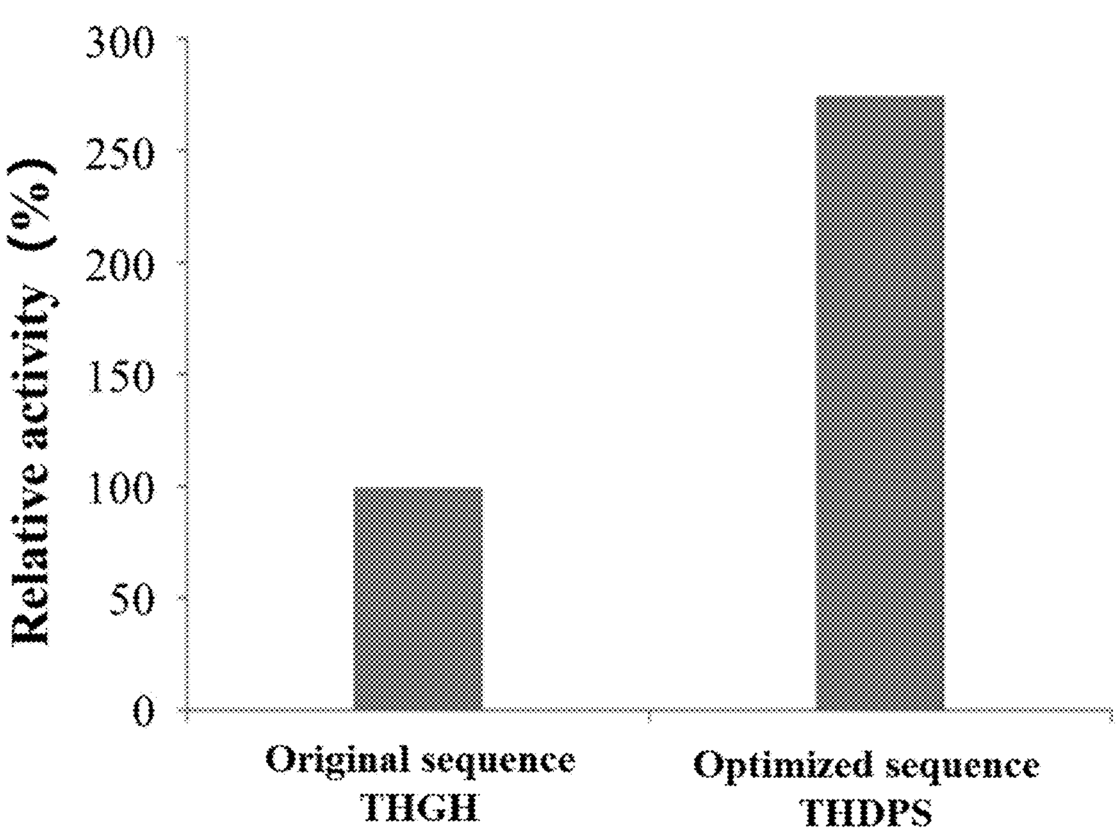
FIG. 2 shows the relative activity of glycosidases before and after sequence optimization.

Meanwhile, in order to further improve the expression level and enzymatic activity of THGH protein, codons were optimized by taking a THGH gene sequence in *T. halotolerans* as a template according to the degeneracy of host codons of *E. coli* to synthesize a ThDPS gene (the nucleotide sequence is as shown in SEQ ID NO.2) with a size of 1326 bp. Homologous recombinant primers ThDPS-21AF (5'-AAGAAGGAGATATACATATGCGTAAACGCCTGACCGTG-3', as shown in SEQ ID NO.7) and ThDPS-21AR (5'-CAGTGGTGGTGGTGGTGGTGATCGGTGGTGCAGGTCAGGGTC-3', as shown in SEQ ID NO.8) were designed. A 6× His-tag downstream of recombinant protein was retained. Seamless cloning was carried out on a prepared gene fragment product and pET21a empty plasmid (double enzyme digestion with NdeI and XhoI), and ligation products were transformed into *E. coli* BL21 (DE3), and after sequencing was carried out to verify the correctness, the expression is induced according to the method in Example 1. The enzymatic activity analysis of hydrolyzed *Dendrobium* polysaccharides was carried out on expression products optimized by codons. The results are shown in FIG. 2. Compared with the THGH expression enzymatic activity level without codon optimization (68 U/OD bacterial cells), the optimized sequence ThDPS expression enzymatic activity level was significantly increased by 2.75 times, reaching 187 U/OD bacterial cells, laying a technical foundation for the subsequent high-level preparation of *Dendrobium* polysaccharide hydrolases.

Figure 3:
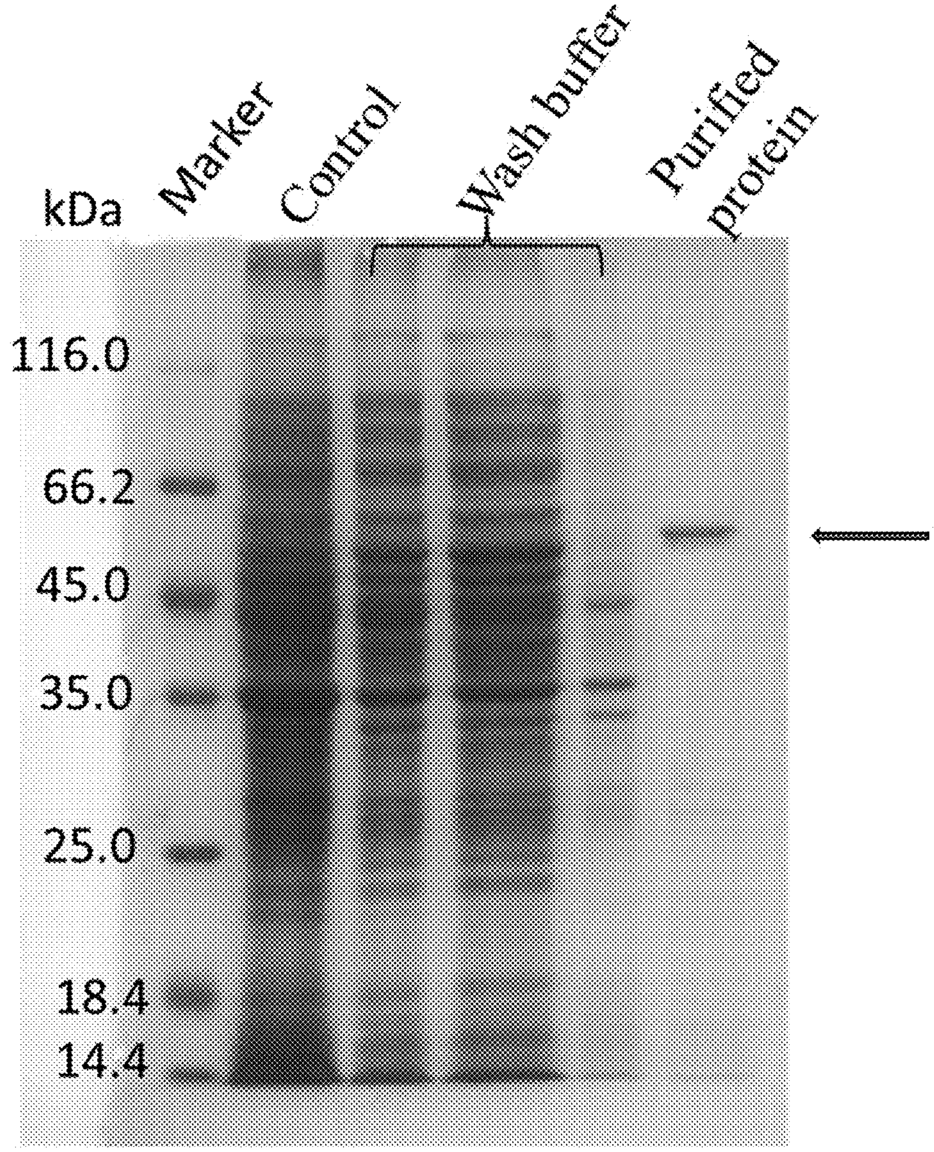
FIG. 3 shows an electropherogram of ThDPS recombinant protein expression and protein purification.

Example 3: Purification and Enzymatic Activity Characterization of ThDPS *Dendrobium* Polysaccharide Hydrolases The enzyme solution prepared in Example 2 was collected, protein purification was carried out with a nickel column to prepare ThDPS enzymes, and the enzymes were stored in a refrigerator at −20° C. for later use. By SDS-PAGE protein electrophoresis, as shown in FIG. 3, purified protein bands are about 50-52 kDa in size, being basically consistent with the theoretical size.

By taking *Dendrobium* polysaccharides as a substrate, the enzymatic property of ThDPS was characterized.

Figure 4:
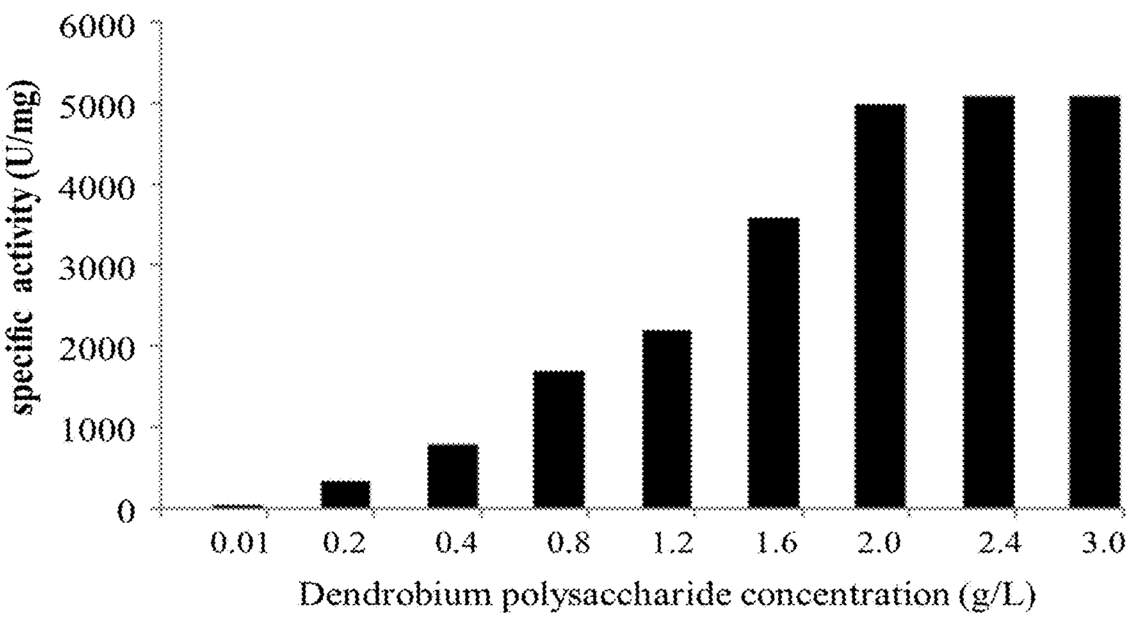
FIG. 4 shows the specific enzymatic activity of ThDPS enzymes in catalyzed hydrolysis of *Dendrobium* polysaccharides at different substrate concentrations.

1. 0.2 g, 0.4 g, 0.8 g, 1.2 g, 1.6 g, 2.0 g, 2.4 g, and 3 g of *Dendrobium* polysaccharides were (Mw>100000 Da) weighed and dissolved in 1 L of distilled water to prepare *Dendrobium* polysaccharide solutions, and then 20 μL of an enzyme solution was added and reacted at 37° C. for 30 min. The enzyme solution was an enzyme solution of ThDPS prepared in Example 2 diluted with deionized water to a concentration of 100 μg/mL. As shown in FIG. 4, as the initial concentration of the *Dendrobium* polysaccharide increased from 0.2 g/L to 3 g/L, the catalytic activity of ThDPS rapidly increased. These results show that there is no significant substrate inhibition in the hydrolysis of *Dendrobium* polysaccharides, and the specific enzymatic activity can reach 5100 U/mg when the substrate concentration is 2.4 g/L.
2. Optimum temperature determination: 10 g/L *Dendrobium* polysaccharides were formulated as a reaction substrate. To a reaction system was added 0.4 mL of *Dendrobium* polysaccharides with a final concentration of 2 g/L, 200 μL of a 500 mM Tris-HCl buffer, and 20 μl of an enzyme solution (providing 10 U of catalytic activity), and 20 μl of distilled water was added to a control group. The water was replenished to a total volume of 2 mL for all reaction solutions. After fair mixing, the mixtures were placed in water baths at 20° C., 30° C., 40° C., 50° C., 60° C., 70° C., 80° C., and 90° C. and incubated for 30 min. The enzyme solution was an enzyme solution of ThDPS prepared in Example 2 diluted with deionized water to a concentration of 100 μg/mL. A DNS-reducing sugar assay was used in the reaction to determine the amount of newly generated reducing sugar in each reaction system.

Figure 5:
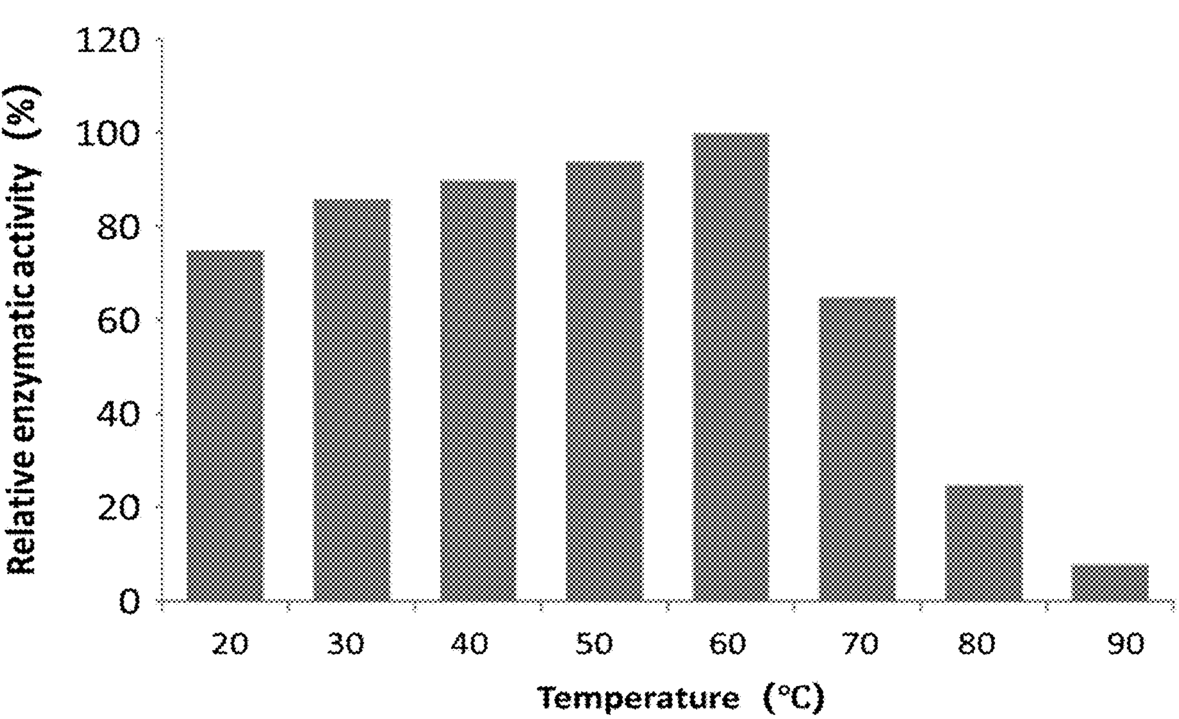
FIG. 5 shows influences of different reaction temperatures on catalyzed hydrolysis of *Dendrobium* polysaccharides with ThDPS enzymes: the relative activity refers to a percentage relative to the maximum reaction enzymatic activity.

According to the results as shown in FIG. 5, ThDPS showed the optimal reaction temperature of 60° C., and its activity was still 85% or more at the temperature between 40° C. and 60° C. This indicates that the enzyme is highly thermally stable. The thermal stability of this *Dendrobium* polysaccharide hydrolase is significantly higher than that of glycosidases from other sources. These results indicate that ThDPS can be used as an excellent high-temperature biocatalytic enzyme for large-scale hydrolysis of *Dendrobium* polysaccharides to prepare low-molecular weight oligosaccharides.

3. Optimum pH Determination:

500 mM buffers with different pHs were prepared: citric acid buffers (pH 2, 3, 4, 5, 6), phosphoric acid buffers (pH 6, 7, 8) and Tris-HCl buffers (pH 8, 9, 10, 11).

10 g/L *Dendrobium* polysaccharides were prepared as a reaction substrate. 0.4 mL of *Dendrobium* polysaccharide sample was added to the reaction system to a final concentration of 2 g/L. The reaction system was supplemented with different pH buffers into 2 mL. 3 tubes were set in each group. 20 μL (50 μg/mL) of an enzyme solution was added to 2 of the tubes, and 20 μL of distilled water was added to the remaining 1 tube. The self-decomposition of the substrate at different pHs was determined, and incubation was carried out at 37° C. for 30 min. After being taken out, the incubated mixed reaction solution was placed in a boiling water bath for 1 min to inactivate the enzymes. 2 mL of a DNS solution was added into each tube, and the tube was placed in the boiling water bath for 3 min, and then was rapidly cooled. The enzyme solution was an enzyme solution of ThDPS prepared in Example 2 diluted with deionized water to a concentration of 100 μg/mL.

Zeroing was performed with deionized water. The absorbance was measured at the wavelength of 540 nm. Referring to a standard curve, the enzymatic activity was calculated. A curve relationship graph between the reaction conditions and the enzymatic activity at different pH values was plotted to determine the optimum pH. The reaction temperature corresponding to the maximum absorption value is the optimum temperature of the recombinant enzyme, and the relative activity (RA) is defined as the percentage of each absorption value to the maximum absorption value.

Figure 6:
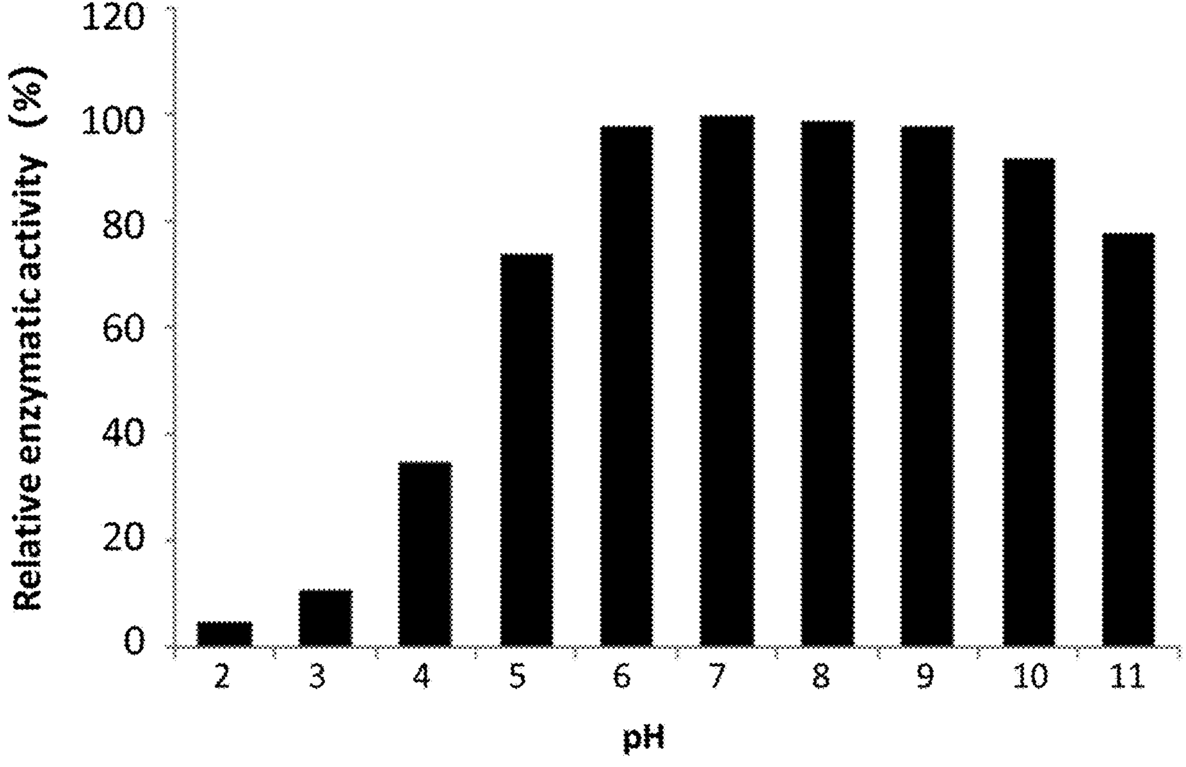
FIG. 6 shows influences of different reaction pHs on catalyzed hydrolysis of *Dendrobium* polysaccharides by ThDPS enzymes: the relative activity refers to a percentage relative to the maximum reaction enzymatic activity.

According to the results as shown in FIG. 6, ThDPS showed maximum activity when it reacted in the 50 mM phosphate buffer of pH 7.0, and showed more than 90% activity in a range of pH 6.0 to 10.0. The results of a pH stability test indicate that ThDPS is also within a wide highly stable pH range, being beneficial for its large-scale catalytic hydrolysis to prepare the *Dendrobium* oligosaccharides.

Example 4: Efficient Preparation of *Dendrobium* Oligosaccharides by Hydrolysis of *Dendrobium* Polysaccharides Using ThDPS Enzyme Solution In order to achieve the maximum hydrolysis efficiency, on the basis of the optimization of the above-mentioned hydrolysis reaction conditions, the concentration of the *Dendrobium* polysaccharides was increased to 10 g/L (with viscosity appearing, the maximum concentration was basically reached) for hydrolysis reaction. 0.1 g of dried *Dendrobium* polysaccharide powder was weighed and dissolved in 10 mL of a phosphate buffer of pH 7.0 to prepare a *Dendrobium* polysaccharide solution, and then 1 ml of an enzyme solution (The concentration of enzyme protein in the enzyme solution was 100 μg/mL) of ThDPS was added and reacted at 60° C. for 2 h. The enzyme solution was an enzyme solution of ThDPS prepared in Example 2 diluted with deionized water to a concentration of 100 μg/mL.

Figure 7:
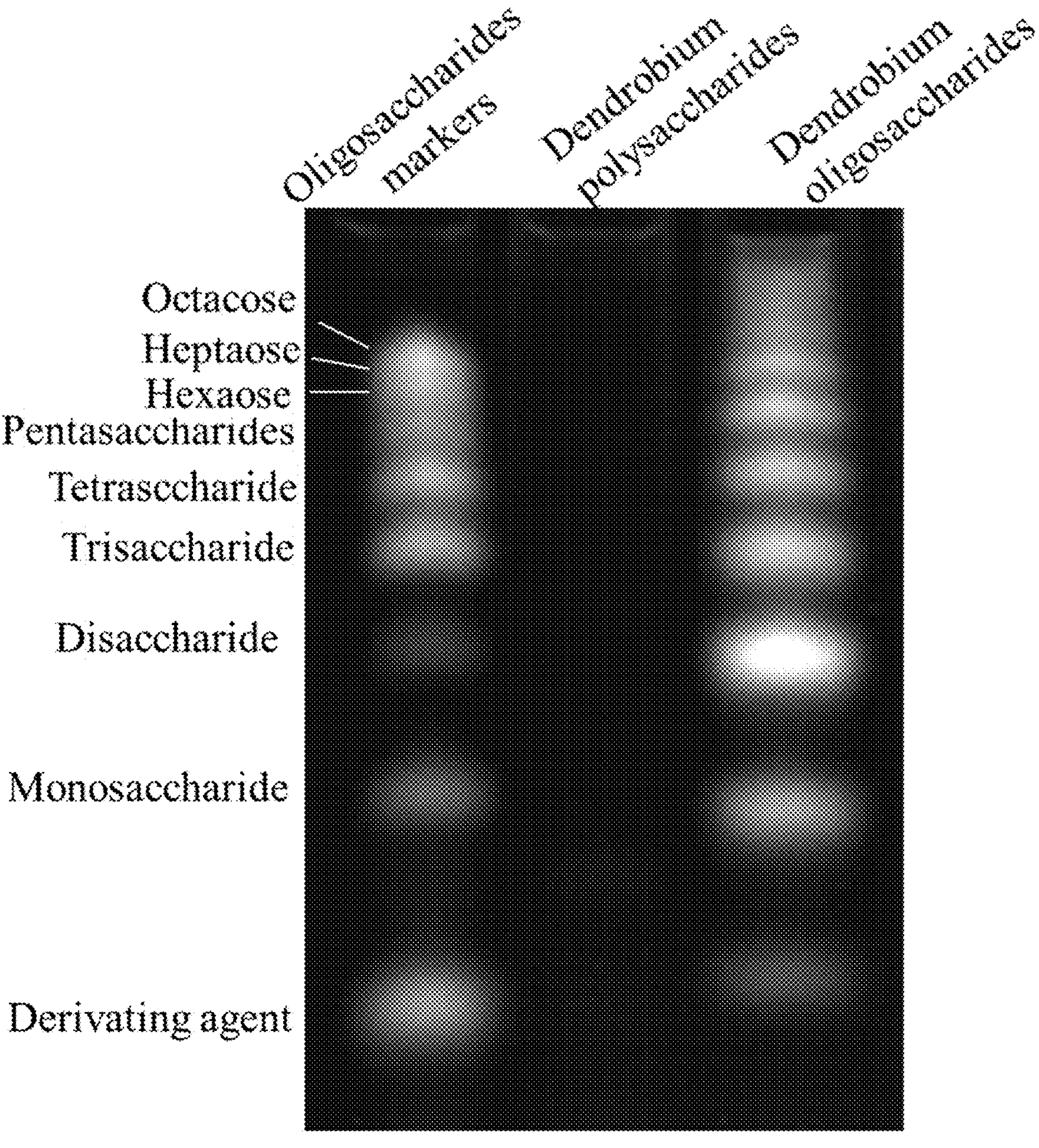
FIG. 7 shows *Dendrobium* oligosaccharide products by catalyzed hydrolysis with ThDPS enzymes detected with fluorescence electrophoresis.

After being subjected to derivatization, the sample was subjected to gel fluorescence electrophoresis. Through observation under a UV lamp, the results are as shown in FIG. 7: with a *Dendrobium* polysaccharide sample solution that is not hydrolyzed with enzymes taken as the control, the ThDPS enzyme solution was added to fully hydrolyze the *Dendrobium* polysaccharides, then the fluorophore-assisted carbohydrate electrophoresis analysis shows that the *Dendrobium* polysaccharide control group does not contain low-molecular weight oligosaccharide products under the same conditions. However, after the *Dendrobium* polysaccharides were hydrolyzed with the ThDPS enzymes, a large amount of ultra-low molecular weight *Dendrobium* disaccharides, *Dendrobium* trisaccharides, *Dendrobium* tetrasaccharides, and *Dendrobium* pentasaccharides, and low-molecular weight *Dendrobium* hexaoses, *Dendrobium* heptaoses, and *Dendrobium* octacoses, and higher *Dendrobium* oligosaccharide products were produced, that is, recombinantly expressed thermophilic mannosidase ThDPS realized efficient hydrolysis of the *Dendrobium* polysaccharide substrate, and ultra-low molecular weight *Dendrobium* oligosaccharide products could be directly prepared in one step.

Figure 8:
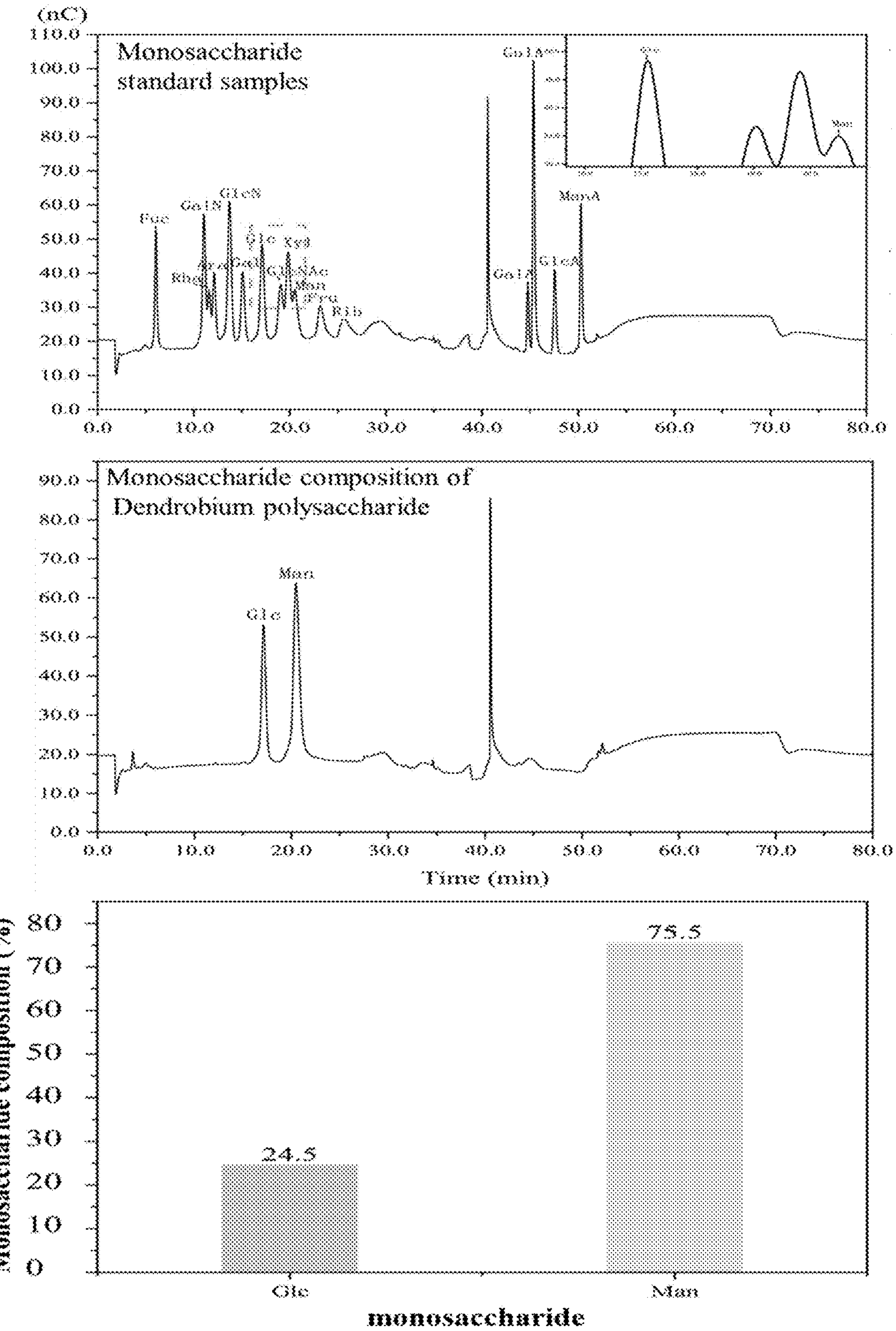
FIG. 8 shows a graph of a monosaccharide composition of *Dendrobium* polysaccharides.

Example 5: Preparation of *Dendrobium* Oligosaccharides Using Hydrolysis with ThDPS Enzymes at Different Times The prepared *Dendrobium* polysaccharide was formulated into a sugar solution with a concentration of 10 g/L. The monosaccharide composition of the *Dendrobium* polysaccharide sample was determined by a monosaccharide determination method, i.e., ion chromatography. The results are as shown in FIG. 8, showing that the *Dendrobium* polysaccharide is composed of two types of monosaccharides: glucose and mannose, respectively, and their molar ratio is 24.5:75.5, indicating that the *Dendrobium* polysaccharide is a type of glucomannan.

0.1 g of dried *Dendrobium* polysaccharide powder was weighed and dissolved in 10 ml of distilled water to formulate 10 mg/ml of a *Dendrobium* polysaccharide solution, and then, the enzyme solution of ThDPS was added in a ratio of 5 μl to 100 mL, and reacted at 37° C. for 0, 45 min, 4.5 h, and 12 h. The hydrolysis was preliminarily determined by DNS. The enzyme solution was an enzyme solution of THDPS prepared in Example 2, where the concentration of enzyme protein in the enzyme solution was 100 μg/mL.

Figure 9:
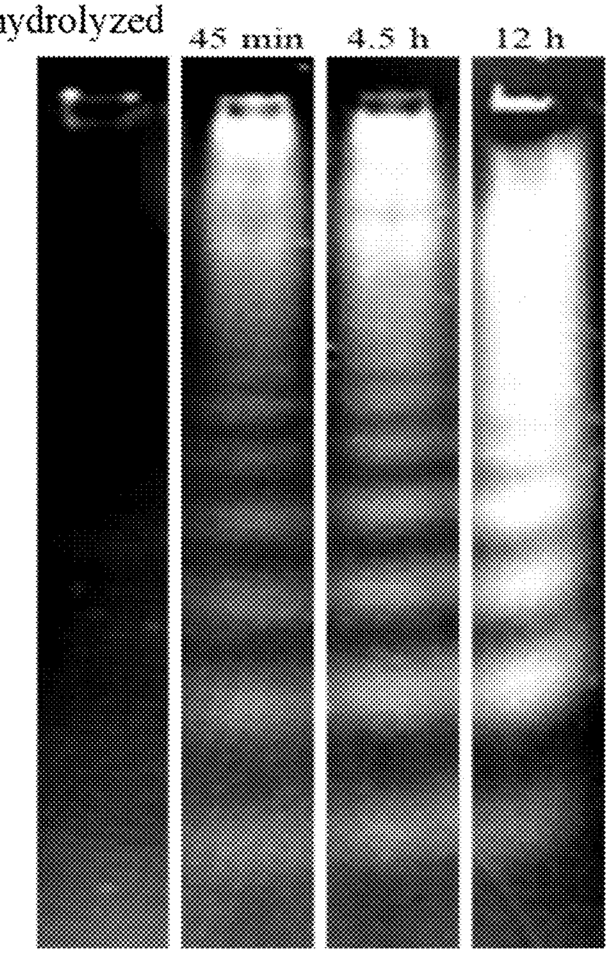
FIG. 9 shows a graph of *Dendrobium* polysaccharide products by hydrolysis with mannosidase THDPS detected with fluorescence electrophoresis.
Figure 10A:
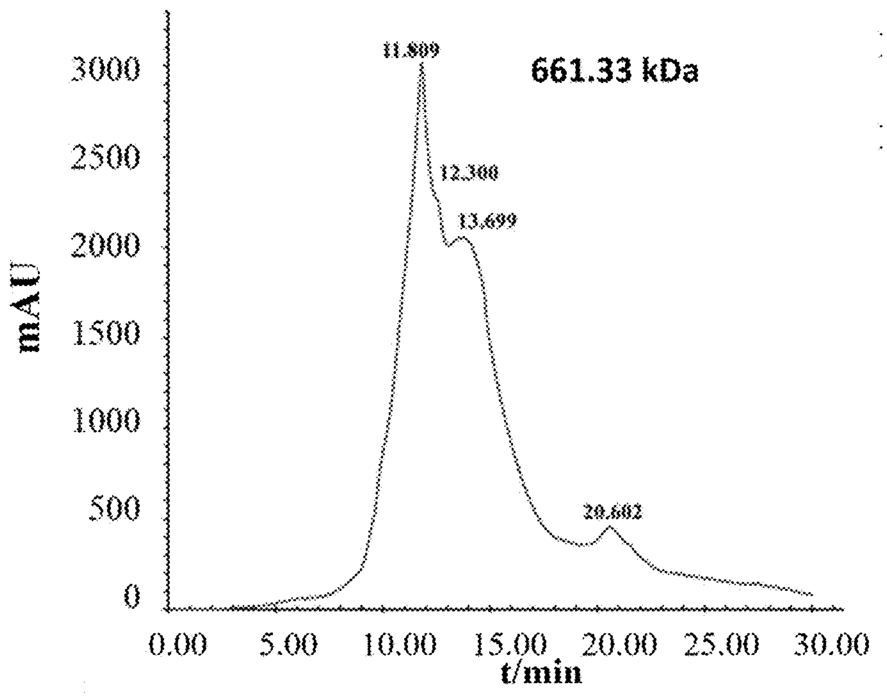
FIG. 10A-10D shows an HPLC graph of *Dendrobium* oligosaccharides hydrolyzed at different times, including a: unhydrolyzed; b: hydrolyzed for 45 min; c: hydrolyzed for 4.5 h; and d: hydrolyzed for 12 h.
Figure 10B:
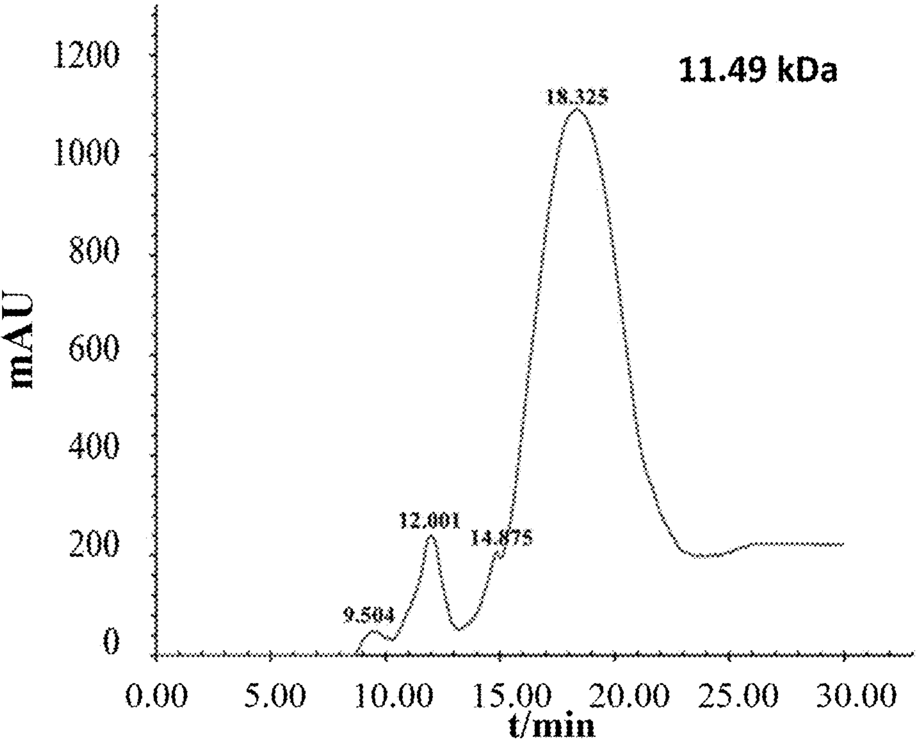
Figure 10C:
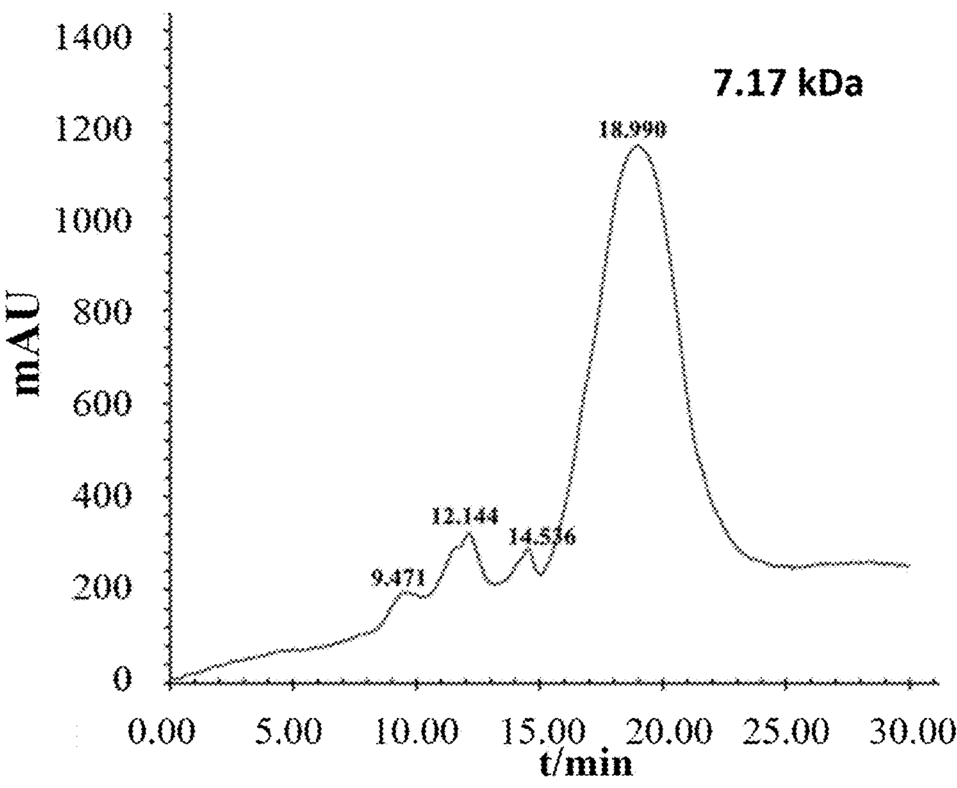
Figure 10D:
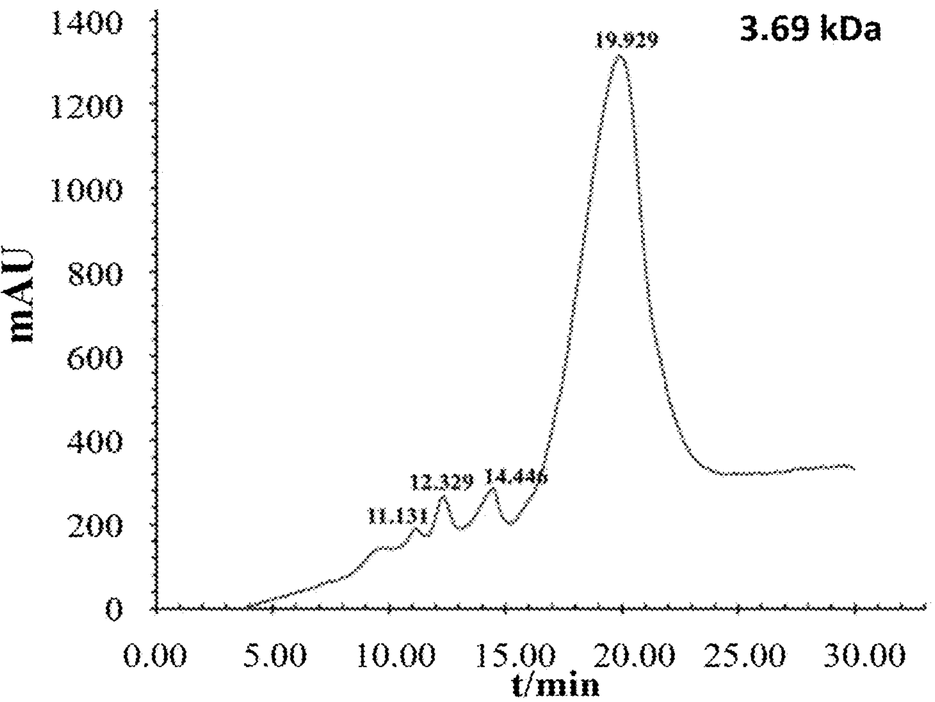

After being treated, the sample was subjected to gel fluorescence electrophoresis. Through observation under a UV lamp, the results are as shown in FIG. 9: with a *Dendrobium* polysaccharide sample solution hydrolyzed with enzymes for 0 min taken as the control, the *Dendrobium* polysaccharides can be hydrolyzed into monosaccharides, disaccharides, trisaccharides and the like after the mannosidase THDPS was added, that is, recombinantly expressed thermophilic mannosidase THDPS realized effective hydrolysis of the *Dendrobium* polysaccharide substrate, and low-molecular weight active mannan oligosaccharides or even monosaccharide products could be directly prepared in one step. The molecular weights of the *Dendrobium* oligosaccharides hydrolyzed at 0 min, 45 min, 4.5 h, and 12 h were determined by liquid chromatography.

The results are as shown in FIG. 10A-10D. It can be seen that with the increase of time, the degree of hydrolysis gradually increases, and the content of oligosaccharides and monosaccharides gradually increases. The results of molecular weight determination are as shown in Table 1.

TABLE 1

Molecular Weight of Hydrolyzed Dendrobium Polysaccharides

| Polysaccharide samples | Retention time (min) | Molecular weight (kDa) |
|---|---|---|
| Unhydrolyzed | 12.60 | 661.33 |
| 45 min | 18.33 | 11.49 |
| 4.5 h | 18.99 | 7.17 |
| 12 h | 19.93 | 3.69 |

Example 6: Proliferative Effect of *Dendrobium* Oligosaccharide Products on Lactic Acid Bacteria Commercial lactic acid bacteria were taken as research objects, including: *L. plantarum* ATCC8014, *S. thermophilus* CICC 6038, *L. reute* ATCC23272, *L. casei* ATCC 393, and *L. rhamnosus* ATCC 53103.

Determination of prebiotics effect of active *Dendrobium* oligosaccharides: the *Dendrobium* oligosaccharides with a molecular weight of 3.69 kDa prepared according to the method of Example 5 and unhydrolyzed *Dendrobium* polysaccharides were added at an addition amount of 0.5% into an M17 medium, being a basal medium of lactic acid bacteria, and an equal amount of sterile water is used as a blank control. The commercial lactic acid bacteria were activated anaerobically twice at 37° C., and then, 100 μL of bacterial solution cultured overnight for about 12 h was sucked and added into a sterilized medium and underwent static culture at 37° C. The absorbance of the bacterial solution, i.e., the OD value at 600 nm at different times was determined to reflect its growth status and demonstrate the prebiotics activity of the *Dendrobium* oligosaccharides.

Figure 11:
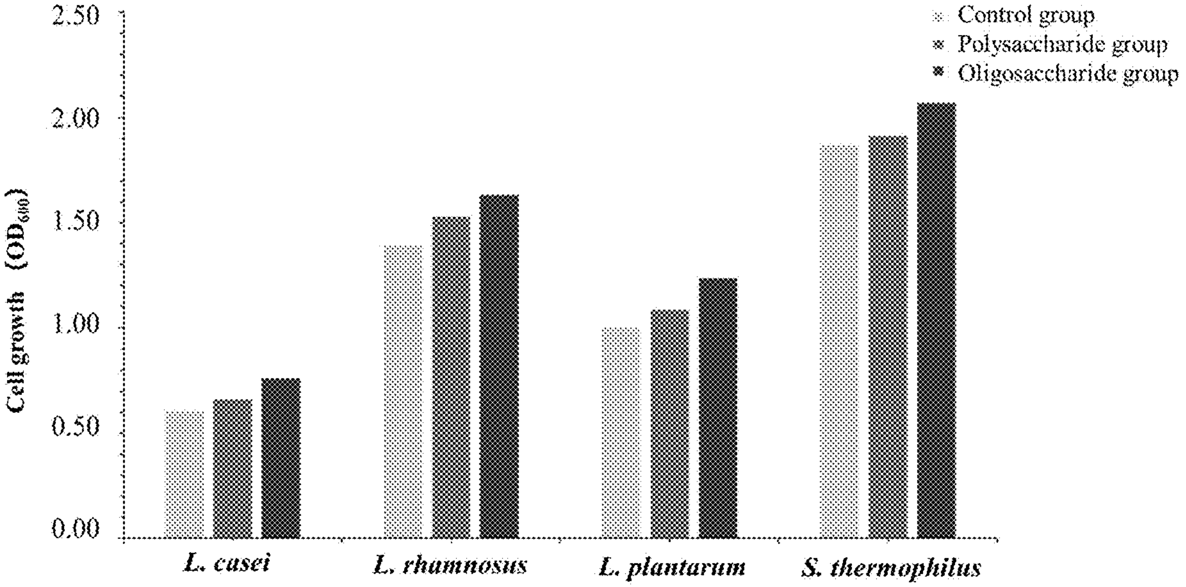
FIG. 11 shows influences of *Dendrobium* polysaccharides and *Dendrobium* oligosaccharides on the proliferative abilities of different groups of strains.
Figure 12:
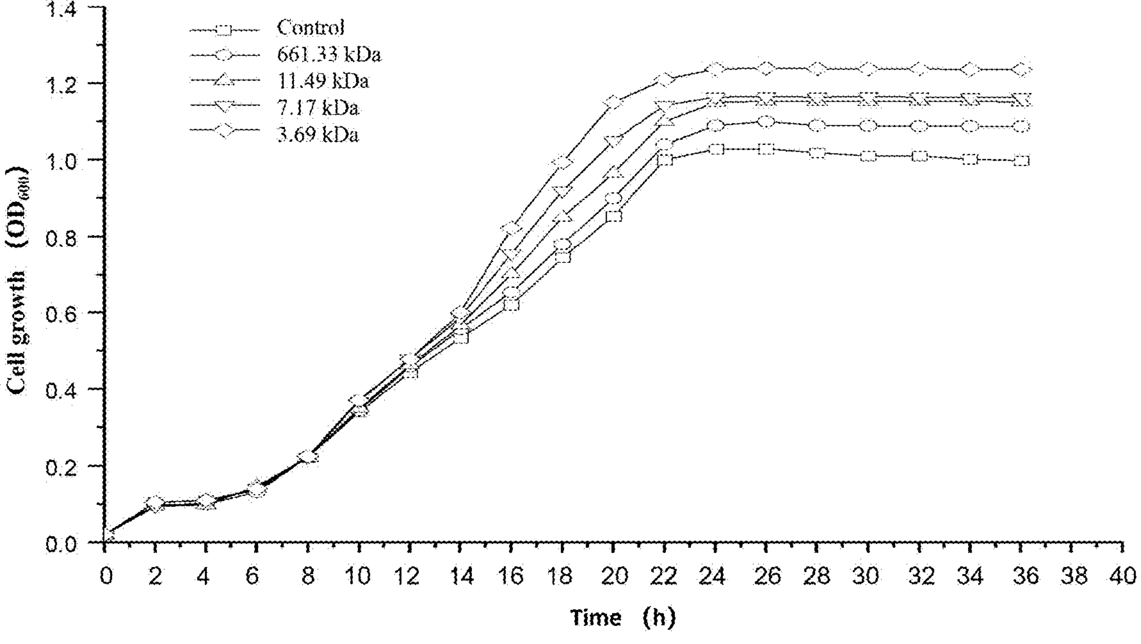
FIG. 12 shows a growth influence curve of *Dendrobium* oligosaccharides of different molecular weights on *L. plantarum*.
Figure 12:
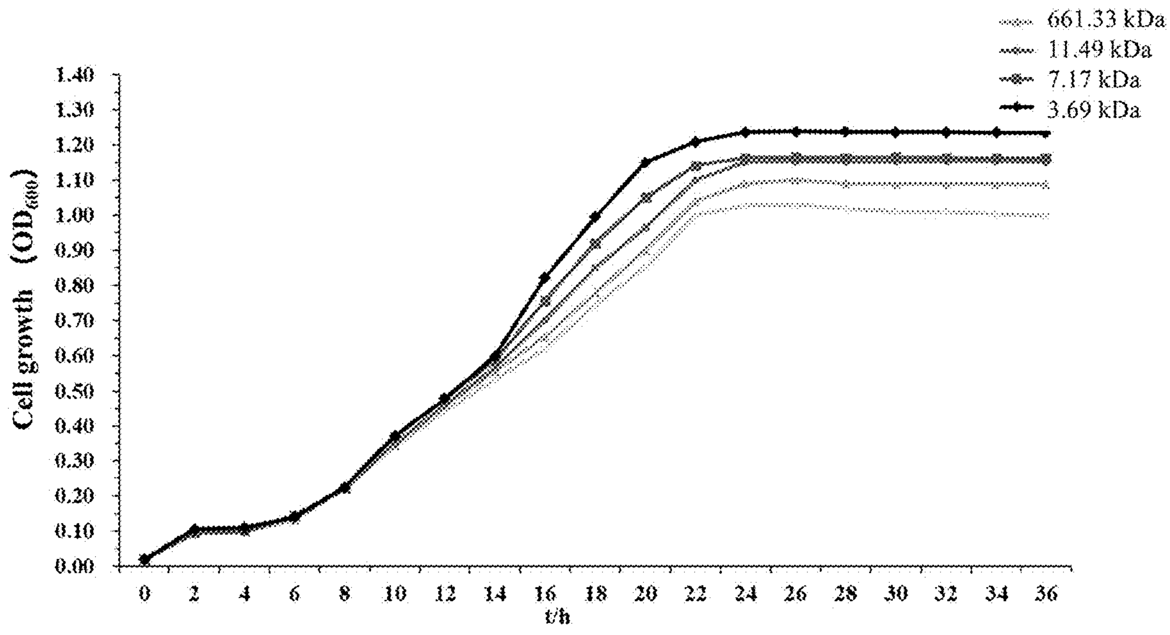

The results are as shown in FIG. 11. The hydrolysis of the *Dendrobium* oligosaccharides for 12 h resulted in a maximum proliferation rate of 34.8% for *L. plantarum* at 20 h of growth. After 36 h of culture, the state remained relatively stable, and the proliferation rate was 23.8%. In this embodiment, the greater the degree of hydrolysis of a *Dendrobium* hydrolyzed sample, the better the proliferation effect on *L. plantarum*, that is, the *Dendrobium* oligosaccharide with a molecular weight of 3.69 kDa obtained after 12 h of hydrolysis has the best proliferation effect on *L. plantarum*. In an experiment, the growth state of *L. plantarum* and the final probiotic effect were relatively stable. Therefore, *L. plantarum* was selected to explore the probiotic effect of the *Dendrobium* oligosaccharide products. The final OD values, i.e., their growth statuses of different probiotics cultured in different culture environments for 36 h were preliminarily determined, as shown in FIG. 12.

Example 7: Exploration of Prebiotics Effect of *Dendrobium* Oligosaccharide Products

*L. plantarum* was cultured by the method in Example 6 as a polysaccharide experimental group. A blank group was not added with 0.5 g/L *Dendrobium* polysaccharides, and an experimental group was added with *Dendrobium* oligosaccharides (the *Dendrobium* oligosaccharides with a molecular weight of 3.69 kDa hydrolyzed for 12 h prepared by the method of Example 5) with a final concentration of 0.5 g/L. The other culture conditions were the same as those of Example 6. The fermentation broth of the strains cultured for 12 h was collected. The bacterial cells were separated from the liquid medium under the condition of 6000×g for 6 min, and the transcriptome sequencing analysis was performed on the bacterial cells, and statistics were made on the differences of gene expression between the two groups. The RNA-seq technical procedure mainly includes two parts: library construction sequencing and data analysis. The library construction sequencing procedure includes: total RNA sample detection→mRNA enrichment→double-stranded cRNA synthesis→terminal repair, addition of A and adapter→fragment selection and PCR amplification→library construction→Illumina sequencing. Afterwards, data analysis was conducted. Due to the influence of sequencing depth and gene length, the gene expression value of RNA-seq is generally not expressed by read count, but by FPKM, correcting the sequencing depth and gene length successively. The expression genes of the two groups were compared, and the statistical results of some differentially expressed genes obtained are shown in Table 2. The genes related to fatty acid synthesis include Ip_1670, Ip_1675 and Ip_0159. The supernatants of the liquid mediums of the blank control group, the *Dendrobium* oligosaccharide experimental group and the unhydrolyzed *Dendrobium* polysaccharide experimental group were retained, and the changes of fatty acids and other components were determined by GC-MS. The results show that there are significantly differences between the experimental group added with the *Dendrobium* oligosaccharide sample the control group and between the experimental group added with the *Dendrobium* polysaccharides and the control group in the content of some of short-chain fatty acids.

TABLE 2

Differences in Content of Short-chain Fatty Acids of Strains under Different Fermentation Conditions (unit: μg/mL)

| Group | Acetic acid | Propionic acid | Isobutyric acid | Butyric acid | Isovaleric acid | Caproic acid |
|---|---|---|---|---|---|---|
| Blank group | 256.892 | 3.193 | 1.653 | 0.696 | 1.298 | 0.040 |
| Oligosaccharide group | 273.998 | 2.990 | 1.518 | 0.697 | 1.191 | 0.029 |
| Polysaccharide group | 455.610 | 5.105 | 2.507 | 1.127 | 1.931 | 0.069 |

TABLE 3

Differences in Gene Expression of Strains under Different Fermentation Environments

| Gene | Gene description | Fold Change FC*in LPE |
|---|---|---|
| Ip_1677 | (3R)-hydroxymyristoyl-[acyl carrier protein] dehydratase FabA-like domain | 4.711 |
| Ip_1681 | Enoyl-(acyl carrier protein) reductase | 4.223 |
| lp_1671 | 3-Oxoacyl-[acyl-carrier-protein (ACP)] synthase III | 2.843 |
| Ip_1673 | [Acyl carrier protein] S-malonyltransferase acyl transferase domain | 2.828 |
| lp_1670 | (3R)-hydroxyacyl-[acyl carrier protein] dehydratase FabA-like domain | 2.495 |
| lp_0159 | Short chain dehydrogenase/oxidoreductase | 0.697 |

Note:

Compared with a control culture growing in M17, the difference of gene expression is estimated as a fold change (FC) in mRNA encoding corresponding protein after 12 h of culture of strains under the stimulation of 5% (v/v) Dendrobium oligosaccharides.

Although the disclosure has been disclosed with preferred examples, it is not intended to limit the disclosure. Anyone familiar with this technology, without departing from the spirit and scope of the disclosure, can make various changes and modifications. Therefore, the scope of protection of the disclosure should be based on the scope defined in Claims.

What is claimed is:

1. A method for hydrolyzing Dendrobium polysaccharides, comprising hydrolyzing Dendrobium polysaccharides in a Dendrobium polysaccharide-containing solution system with a Thermobifida *halotolerans*-derived glycosidase or a recombinant microorganism expressing the glycosidase, the glycosidase having an amino acid sequence shown in SEQ ID NO:3.

2. The method according to claim 1, wherein a gene encoding the glycosidase has a nucleotide sequence set forth in SEQ ID NO:1 or SEQ ID NO:2.

3. The method according to claim 1, wherein the glycosidase is present in an amount of ≥1 U/g Dendrobium polysaccharide.

4. The method according to claim 1, wherein the recombinant microorganism comprises *Escherichia coli*.

5. The method according to claim 4, wherein the recombinant microorganism comprises *E. coli* BL21 (DE3) and pET21a as an expression vector.

6. A method for preparing ultra-low molecular weight Dendrobium oligosaccharides, comprising degrading Dendrobium polysaccharides with a glycosidase with an amino acid sequence as shown in SEQ ID NO:3 or a cell culture containing the glycosidase; wherein the molecular weight of the ultra-low molecular weight Dendrobium oligosaccharide is ≤1000 Da and the oligosaccharides include Dendrobium disaccharides, Dendrobium trisaccharides, and Dendrobium tetrasaccharides.

7. The method according to claim 6, wherein the glycosidase or the cell culture containing the glycosidase is added to a Dendrobium polysaccharide-containing reaction system; and the the glycosidase is present in an amount of ≥1 U/g Dendrobium polysaccharide.

8. The method according to claim 7, wherein the amount of the glycosidase is 1-1000 U/g Dendrobium polysaccharide.

9. The method according to claim 8, wherein a pH value of a solution in the reaction system is controlled to be 5.0-10.0, and the reaction temperature is 10° C.-75° C.

10. The method according to claim 6, wherein the cell culture is a glycosidase-containing fermentation broth obtained by culturing a recombinant microorganism expressing the glycosidase in a medium for a period of time.

11. A recombinant *E. coli* BL21 (DE3) host cell expressing a glycosidase gene with a nucleotide sequence as set forth in SEQ ID NO:1 or SEQ ID NO:2 in a pET21a expression vector.

* * * * *

SEQUENCE LISTING

```
Sequence total quantity: 8
SEQ ID NO: 1            moltype = DNA  length = 1326
FEATURE                 Location/Qualifiers
source                  1..1326
                        mol_type = other DNA
                        organism = Thermobifida halotolerans
SEQUENCE: 1
atgagaaaac gtctcacggt cgccgcggcg acgattctcg cgctgctcgc gtccgtcttc  60
gtgttcgcgc aaccggcgaa cgcggccacc ggcttctacg tcgacaacgg tcggctctac  120
gaggcgggcg gccaggagtt cgtcatccgc ggcgtcagcc acccccacgc ctggtacgcg  180
caggagaccg actccttcgc gggcatcaag tcccacggcg ccaacaccgt gcgcgtggtg  240
ctgagcaacg gcgtccggtg gaccaagaac gacgccgccg acgtcgccaa cgtcatctcc  300
ctgtgcaagc agaaccggct catctgcatg ctggaggtgc acgacaccac cggctacggc  360
gagcagagcg gcgcctccac cctcgaccag gccgtcgact actggatcga gatccaaagc  420
gccctggagg gccaggagga ctacgtcctc atcaacatcg gcaacgagcc ctacggcaac  480
gactccgcca ccgtcgccga ctgggcctcc gacacctccg ccgccatcca gcggatgcgc  540
gacgccgggt tcgaccacac cctcgtggtg gacgcccccca actggggcca ggactggtcg  600
cacaccatgc gcgacaacgc cggcagcgtc tacaccagcg acccgaccgg caacacggtc  660
ttctccatcc acatgtacgg cgtctacgag cagggctcca cggtcaccag ctacctggag  720
cacttcgtca acgccggtct gccgatcatg atcggcgagt tcggccacga ccactccgac  780
ggcaaccccg acgaggacac catcatggcc gaggccgagc ggctgggcct gggctacatc  840
ggctggtcgt ggagcggcaa cggcggcggc gtcgagtacc tggacatggt gaacaacttc  900
gacgccgaca gcctgacctc gtggggccag cggatcttct acggtgccaa cggcatctcc  960
agcaccgccg aggaggccac cgtctacggc ggggggggcgc ccacggaccc gccgaccgac  1020
ccgcccgccg agggcgactg ctcggccgac tacaccacgg tcggaagctg gggcggcggc  1080
ttccagggcg aggtcacggt caccgcgggc gactcggcca tctccaactg gacggtgagc  1140
tggaccttcc ccggtggcca gagcgtcagc cacggctgga acgccagctt cggcggcggc  1200
tccccggtca cggcgagcaa cgctccctac aacggacagc tcggcgccgg acagtccacc  1260
acgttcggct tcatcggctc gggcagtgcc cccggatcgc tgacgctgac ctgcaccacc  1320
gactga                                                             1326

SEQ ID NO: 2            moltype = DNA  length = 1326
FEATURE                 Location/Qualifiers
source                  1..1326
                        mol_type = other DNA
                        organism = synthetic construct
SEQUENCE: 2
atgcgtaaac gcctgaccgt ggccgccgca acgattctgg ccctgctggc cagcgtgttt  60
gtgtttgccc agccggcgaa tgcggcgacc ggtttttacg tggataacgg ccgtctgtac  120
gaagcgggcg gccaagaatt tgtgattcgt ggtgtgagcc acccgcacgc gtggtatgcg  180
caggaaaccg atagctttgc aggtattaaa agccatggcg cgaataccgt gcgcgttgtg  240
ctgtctaatg gcgtgcgttg gaccaaaaat gatgccgcgg atgtggccaa tgtgatctcg  300
ctgtgtaaac agaatcgcct gatttgtatg ctggaagtcc atgataccac cggatacggc  360
gagcagagcg gcgcgagcac cctggatcag gccgtggatt attggattga aattcagagc  420
gcgctggaag gccaggaaga ctatgtgctg attaacatcg gcaacgaacc gtatggcaac  480
gactcggcca ccgtggccga ttgggcgtca gataccagcg cggcgattca gcgcatgcgc  540
gatgccggct ttgatcatac cctggtggtg gatgccccga actggggcca ggattggtct  600
cacacgatgc gcgataatgc gggtagcgtg tacaccagcg atccgaccgg caacaccgtg  660
ttcagcatcc acatgtatgg cgtgtatgaa cagggcagca ccgtgaccag ctatctggaa  720
cactttgtta atgcgggtct gccgattatg attggcgaat ttggtcacga tcatagcgat  780
ggcaacccgg atgaagatac cattatggcc gaagcggaac gtctgggcct gggctatatt  840
ggctggagct ggagcggcaa cggcggcggc gtggaatatc tggatatggt gaataacttt  900
gacgcggata gcctgaccag ctggggtcag cgtatttttt acggcgcgaa cggcatcagc  960
agcaccgcgg aagaagcgac cgtgtatggc ggcggcgcgc cgaccgatcc gccgaccgat  1020
ccgccggcgg aaggcgattg cagcgcggac tataccaccg tcggcagctg gggcggcggc  1080
ttccagggcg aagtcaccgt cacagcgggc gatagcgcga tttctaattg gaccgtgagc  1140
tggacctttc cgggcggcca gagcgttagc catggctgga acgccagctt tggcggcggc  1200
agcccggtta ccgccagcaa cgccccgtat aacggccagc tgggcgcggg tcagagcacc  1260
acctttggct ttattggcag cggcagcgcg ccgggcagcc tgaccctgac ctgcaccacc  1320
gattga                                                             1326

SEQ ID NO: 3            moltype = AA  length = 441
FEATURE                 Location/Qualifiers
source                  1..441
                        mol_type = protein
                        organism = Thermobifida halotolerans
SEQUENCE: 3
MRKRLTVAAA TILALLASVF VFAQPANAAT GFYVDNGRLY EAGGQEFVIR GVSHPHAWYA  60
QETDSFAGIK SHGANTVRVV LSNGVRWTKN DAADVANVIS LCKQNRLICM LEVHDTTGYG  120
EQSGASTLDQ AVDYWIEIQS ALEGQEDYVL INIGNEPYGN DSATVADWAS DTSAAIQRMR  180
DAGFDHTLVV DAPNWGQDWS HTMRDNAGSV YTSDPTGNTV FSIHMYGVYE QGSTVTSYLE  240
HFVNAGLPIM IGEFGHDHSD GNPDEDTIMA EAERLGLGYI GWSWSGNGGG VEYLDMVNNF  300
DADSLTSWGQ RIFYGANGIS STAEEATVYG GGAPTDPPTD PPAEGDCSAD YTTVGSWGGG  360
FQGEVTVTAG DSAISNWTVS WTFPGGQSVS HGWNASFGGG SPVTASNAPY NGQLGAGQST  420
TFGFIGSGSA PGSLTLTCTT D                                            441

SEQ ID NO: 4            moltype = DNA  length = 1362
FEATURE                 Location/Qualifiers
```

```
source                  1..1362
                        mol_type = other DNA
                        organism = Thermobifida fusca
SEQUENCE: 4
atgagaaaac gtctcgcggt cgccgcagca accgtccttg cgctgctggc gtccgtcttt  60
gccctcacgc agccggcgaa cgcggccacc gggctccacg tcaagaacgg ccgcctgtat  120
gaggccaacg gccaggagtt catcatccgt ggcgtcagcc acccccacaa ctggtacccc  180
cagcacaccc aggcgttcgc cgacatcaag tcgcacggcg ccaacaccgt ccgggtggtg  240
ctgagcaacg gtgtccggtg gagcaagaac ggtccttctg acgtcgccaa cgtcatctcc  300
ctgtgcaagc agaaccgcct tatctgcatg ctggaggtgc acgacaccac cggctacggc  360
gagcagagcg gggcctccac gctcgaccag gccgtcgact actggatcga gctgaagagc  420
gtgctccagg gcgaggagga ctatgtcctc atcaacatcg gcaacgagcc ctacggcaac  480
gactccgcga ccgtcgcccg ctgggcgtcg gacacctccg ccgccatcca gcggctgcgc  540
gccgccggat tcgagcacac cctcgtggtg gacgccccca actggggcca ggactggacg  600
aacaccatgc ggaacaacgc cgaccaggtg tacgccagcg accccaccgg caacaccgtc  660
ttctcgatcc acatgtacgg cgtctactcc caggcgtcca cgatcgccag ctacctggag  720
cacttcgtca acgcgggcct gccgctcatc atcggcgagt tcggccacga ccactccgac  780
ggcaaccccg acgaggacac gatcatggcc gaggccgagc ggctcaagct gggctacatc  840
ggctggtcgt ggagcggcaa cggcggcggg gtcgagtacc tcgacatggt gtacaacttc  900
gacggcgaca acctgagccc gtggggcgag cggatcttct acggccctaa cggtattgcg  960
agcacggcca aggaggccac gatcttcggc ggctcccagc cgggcccgac cgaggagccg  1020
acggaagagc cgaccgagga gccgactccg actccgcctc ccgcggaggg cgactgcacc  1080
gccacctacg ccaccatcgg cagctggggc ggcggcttcc agggtgaggt gacggtcacc  1140
gcgggcgact ccgcgatctc ctcgtggcag gtgagctgga ccttccccgg cggccagagc  1200
gtggcccacg gctggaacgc cagcttcagc ggcacgagca cggtgacggc cagcaacctg  1260
tcctacaacg gccagctggg tgcgggacag tccgccacgt tcggcttcat cggctcgggc  1320
gacgcgccta gctcgctgac gctgagctgc accgctcgct ga                    1362

SEQ ID NO: 5            moltype = DNA  length = 2193
FEATURE                 Location/Qualifiers
source                  1..2193
                        mol_type = other DNA
                        organism = Klebsiella pneumoniae
SEQUENCE: 5
atgaagccga tgaaaaactt gctgctgatg ggctgctgt ccgcgctggc ggccggcggg  60
gcgctggccg ccgagcgctc gcactttacg cactttatca ctcgcgacgg cgccaccctc  120
aaggacggcg acaaggtgtt tcgtttcgcc gggatccacg cgccggagct gcaccgcatt  180
gaagacgacg cccgcggccc ctgcagggca gacccgcgcg gctgggggca atactttaaa  240
tggccaacgg cccaggagca gcaaaactgg atccaggcga tggtgcaaac cggggcgaaa  300
gcccagcgcg tctacgtgct gtcggtgcag caggaatttg ataaggcctg cgggcgcgag  360
acccatattc tggcgccgga aacggcggac ggcatgccgc ggctgaatga gaaagccatg  420
cgggtgtatg acaacatgat tgccgaagcg gataaacagg gattgcgtct gatcctgccg  480
tttatcgacc actggtggtg gtggggcggg cgcgagcagc tggcggcgtt ctatcatgaa  540
aaagcggaag acttttatcg gaccgatagc aagaccttca aagcctatct ggatgtgatc  600
cgccaggtca tcacccggac aaataccgtc accggccgcg cctattatga tgaaaaggcg  660
atcatggcct gggaaaccgg taacgagctg gaggatacca acgccgattt cctgcatcag  720
accgcggcgt ggattaaaaa gtgggcccct catcagctgg tggtggatgg cacctataag  780
aaaattaatc cgtttgcgtt gaccgacccc aatgtggata tcgtcagcaa tcactattac  840
accaatgccg ataataacca tcccgggcag gtgacgcagg atctgcgcgc cgtcggcgga  900
caaaaagtct atctcgtcgg cgagtttggc ctgctgccgg cggatcaact gaacgccatt  960
atgcagtcga ttgttcacag cgaggtcaac ggggcgcaag ccgccggcgg gcttatctgg  1020
ggcttccgcg gccatcgtca cgacggcggc ttctactggc ataaggagtc gaccgggcac  1080
tatagctacc acctgccggg gtttgccaaa gaaggcgaag cgaaccagga gcaggcggtg  1140
gtcgatctgg tgcgcaccgc cgcggcgcag atggccgggc agcagacgat ggcaccgctg  1200
ccgaagccgg acgcgccttt gctgcgcgaa accacctcgc ccttcgcgat caactggatg  1260
ggcgctgcgg tgggacgcag ctacgatgtc gaacgcgccg cctcaccgac cgggccgtgg  1320
acggtggtgg gccgggatat ctccgatggc gttaacgaat ggaatccgga aaccatggtt  1380
ctgttccgcg acgattatcg tcagcttcag ctcgggcaca cgtattacta ccgggtgacg  1440
gcgaaaaacg agagtggtcg ttcggcccct tccaatgtga ttagcgtgca gcatagcgag  1500
gagaatcagc caccggttgt cacgctggaa ccggccctaa ccaccacgca ggaccagggc  1560
gtcgagctta cggccagctg gcaggacgat ggcctgccgt cgcgagaggt taaggtgggc  1620
tggcagcacg ccggcgatgg ccaggtgcat ttctgccatg ccgatcgggc tcaaacccgg  1680
gcctggttta cgacgccagg tacctatgcg ctgacgttca cggcggacga tgggctgttg  1740
aaaagcagca aaaccgtgac cgtgacggta ggcgaggcgg cggggaaagc gccagcggat  1800
ttctgtcgtt atcacggcga agtttatggc gtggctgagg ggcggctgac ggtgatgaag  1860
agtgataaag acgcgctggc agttggcgag gacggcttcc tcggcccatt tgccaacgag  1920
ggggataagg tcagctggca ggtgcaggcg ccgtggagcg gtcagttcct gctcaatgta  1980
accttcaacg gcaaatgggg cggtaagcag aactcatttg tcgtcaacgg gggcgctccg  2040
cagaccgtgg ccttcccgca gacggatgag cagggccagc agctgcggat accggtgacg  2100
cttaaagccg ggagcaatca gattgacttc ggccgcttcg ccggcgactg ggctatatg  2160
ttcattaaat cgatcgaagt ggtcgctgag tag                              2193

SEQ ID NO: 6            moltype = DNA  length = 1365
FEATURE                 Location/Qualifiers
source                  1..1365
                        mol_type = other DNA
                        organism = Thermobifida alba
```

-continued

```
SEQUENCE: 6
atgagaaaac gtctcgcggt cgcggcagcg acgattctcg cgctgctcgc ctccgtcttc  60
gtcatcgcgc agcccgccag cgctgccacc ggtctgcatg tccacaatgg acggctctac  120
gaggccaacg gccaggagtt catcatccgt ggcgtcagcc acccccacaa ctggttcccc  180
cagcacaccg gcgccttcgc cgacatcaag tcgcacgggg ccaacaccgt gcgcgtggtg  240
ctgagcaacg gcgtccgctg ggccaagaac ggcccctccg acgtcgccaa cgtcatctcc  300
ctgtgcaagc agaaccacct catctgcatg ctggaggtgc acgacaccac cggctacggg  360
gaggagggcg cagcctccac cctcgaccag gccgtcgact actggatcga gctgaagagc  420
gtgctgcagg gcgaggagga ctacgtcctg atcaacatcg gcaaggagcc ctacggcaac  480
aacgccgcca cggtggccga ctgggcctcc gacacctccg ccgccatcca gcggctgcgc  540
agcgagggct tcgaccacac cctcgtcgtg gacgccccca actggggcca ggactggtcg  600
cacaccatgc gtgacaacgc cgccggggtc tacgccagcg acccgaccgg caacaccgtc  660
ttctcgatcc acatgtacgg cgtctactcg cagggcgcca cggtcaccag ctacctggag  720
cacttcgtca acgccggcct gccgatcatg atcggcgagt tcggccacga ccactccgac  780
ggcaaccccg acgaggacac catcatggcc gaggccgagc ggctgcgcct gggctacatc  840
ggctggtcgt ggagcggcaa cggcggcggt gtcgagtacc tggacatggt caacaacttc  900
gacggcgaca gcctgacccc gtgggggcag cggatcttct acggtcctca cggcatctcc  960
agcaccgccc aggaggccac gatctacggt ggtagcccgg gcccgactcc cgacccgacc  1020
ccggacccga ctcccgaccc gactcccgac cccgacccgg gcaccgagcc gggcgactgc  1080
acggccgcct acaccaccat cggcagctgg ggcggcggct tccagggcga ggtcacggtc  1140
accgcgggcg actccgccat ctccaactgg acggtgaact ggaccttccc cggcggccag  1200
accgtcagcc agggctggaa cgccagcttc agcggcagca gctcggtcac ggccagcaac  1260
gtgtcctaca acggccagct gggcgctggg cagtccacca cgttcggctt catcggctcg  1320
ggcagcgctc ccgggtcgct gacgctgagc tgcacgaccg actga                 1365

SEQ ID NO: 7            moltype = DNA  length = 38
FEATURE                 Location/Qualifiers
source                  1..38
                        mol_type = other DNA
                        organism = synthetic construct
SEQUENCE: 7
aagaaggaga tatacatatg cgtaaacgcc tgaccgtg                          38

SEQ ID NO: 8            moltype = DNA  length = 42
FEATURE                 Location/Qualifiers
source                  1..42
                        mol_type = other DNA
                        organism = synthetic construct
SEQUENCE: 8
cagtggtggt ggtggtggtg atcggtggtg caggtcaggg tc                     42
```